US008946302B2

(12) United States Patent (10) Patent No.: US 8,946,302 B2
Ruoho et al. (45) Date of Patent: Feb. 3, 2015

(54) SELECTIVE SIGMA-1 RECEPTOR LIGANDS

(71) Applicant: Wisconsin Alumni Research Foundation, Madison, WI (US)

(72) Inventors: Arnold E. Ruoho, Madison, WI (US); Abdol R. Hajipour, Madison, WI (US); Uyen B. Chu, Madison, WI (US); Dominique A. Fontanilla, Twickenham (GB)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/707,418

(22) Filed: Dec. 6, 2012

(65) Prior Publication Data

US 2013/0102571 A1 Apr. 25, 2013

Related U.S. Application Data

(63) Continuation of application No. 12/621,246, filed on Nov. 18, 2009, now Pat. No. 8,349,898.

(60) Provisional application No. 61/115,641, filed on Nov. 18, 2008.

(51) Int. Cl.
*A01N 33/02* (2006.01)
*A61K 31/135* (2006.01)
*A01N 33/26* (2006.01)
*A61K 31/655* (2006.01)
*C07C 247/00* (2006.01)
*C07J 41/00* (2006.01)
*C07C 211/00* (2006.01)
*C12N 5/00* (2006.01)
*C12N 5/02* (2006.01)
*C07C 247/16* (2006.01)
*C07C 211/27* (2006.01)
*C07C 211/29* (2006.01)
*C07C 211/49* (2006.01)

(52) U.S. Cl.
CPC ............. *C07C 247/16* (2013.01); *C07C 211/27* (2013.01); *C07C 211/29* (2013.01); *C07C 211/49* (2013.01)
USPC ............... 514/654; 514/151; 522/8; 564/374; 435/375

(58) Field of Classification Search
CPC .. C07C 211/27; C07C 211/29; C07C 211/49; C07C 247/16
USPC ........ 514/151, 654; 552/8; 564/374; 435/375
See application file for complete search history.

(56) References Cited

U.S. PATENT DOCUMENTS 4,277,501 A 7/1981 Molloy et al.
6,482,986 B1 11/2002 Boigegrain et al.

FOREIGN PATENT DOCUMENTS

| CA | 1202636 A * | 1/1986 |
|---|---|---|
| EP | 697407 A1 | 2/1996 |
| FR | 2 846 882 A1 | 5/2004 |
| GB | 1109924 | 4/1968 |
| WO | WO 93/00313 A2 | 1/1993 |
| WO | WO 00/50377 A1 | 8/2000 |
| WO | WO 2006/013048 A1 | 2/2006 |

OTHER PUBLICATIONS

J. G. Cannon, Chapter Nineteen in Burgers Medicinal Chemistry and Drug Discovery, Fifth Edition, vol. I: Principles and Practice, Wiley-Interscience 1995, pp. 783-802, 784.*
Sheridan, R.P. "The Most Common Chemical Replacements in Drug-Like Compounds" J. Chem. Inf. Comput. Sci., 2002, vol. 42, pp. 103-108.*
International Search Report for related International App. No. PCT/US2009/064970 mailed Feb. 18, 2010
Written Opinion for related International App. No. PCT/US2009/064970 mailed Feb. 18, 2010.
Bair et al., "(I-Pryrenylmethyl)amino alcohols, a new class of antitumor DNA intercalators. Discovery and initial amine side chain structure-activity studies," Journal of Medicinal Chemistry (1990) 33 (9): 2385-2393.
Fontanilla et al., "Probing the steroid binding domain-like I (SBDLI) of the Sigma-1 receptor binding site using N-substituted photoaffinity labels," Biochemistry (2008) 47 (27): 7205-7217.
Kumagai et al., "(2R-trans)-2-butyl-5-heptylpyrrolidine as a potent sigma receptor ligand produced by Streptomyces longipororuber," The Journal of Antibiotics (2000) 53 (5): 467-473.
Moebius et al., "High affinity of sigma1-binding sites for sterol isomerization inhibitors: Evidence for a pharmacological relationship with the yeast sterol C8-C7 isomerase," British Journal of Pharmacology (1997) 121: 1-6.
Wilkerson et al., "Anti-inflammatory phospholiphase-A2 inhibitors. II. Design, synthesis and structure-activity relationship," European Journal of Medicinal Chemistry (1992) 27 (6): 595-610.
Ablordeppey et al., "Is a nitrogen atom an important pharmacophoric element in sigma ligand binding?" Bioorganic & Medicinal Chemistry (2000) 8: 2105-2111.
Glennon et al., "Structural features important for sigma-1 receptor building," J. Med. Chem. (1994) 37: 1214-1219.
Glennon et al., "Thioxanthene-derived analogs as sigma-1 receptor ligands," Bioorganic & Medicinal Chemistry Letters (2004) 14: 2217-2230.
Hayashi et al., "An update on the development of drugs for neuropsychiatric disorders: Focusing on the sigma 1 receptor ligand," Expert Opin. Ther. Targets (2008) 12 (1): 45-58.

* cited by examiner

*Primary Examiner* — Kendra D Carter
(74) *Attorney, Agent, or Firm* — Joseph T. Leone, Esq.; Daniel A. Blasiole; DeWitt Ross & Stevens S.C.

(57) ABSTRACT

The invention provides compounds of the formulas described herein and compositions thereof. The invention further provides methods of using the compounds and compositions. The compounds of the invention can provide high affinity binding to sigma-1 receptors in a mammal. The compounds can exhibit selectivity for the sigma-1 receptor over the sigma-2 receptor. The compounds and compositions of the invention can also be used to treat conditions that involve the sigma-1 receptor, such as addiction, cardiovascular conditions, and cancer, for example, cancer of the breast, lung, prostate, ovarian, colorectal, or the CNS.

19 Claims, 12 Drawing Sheets

A.
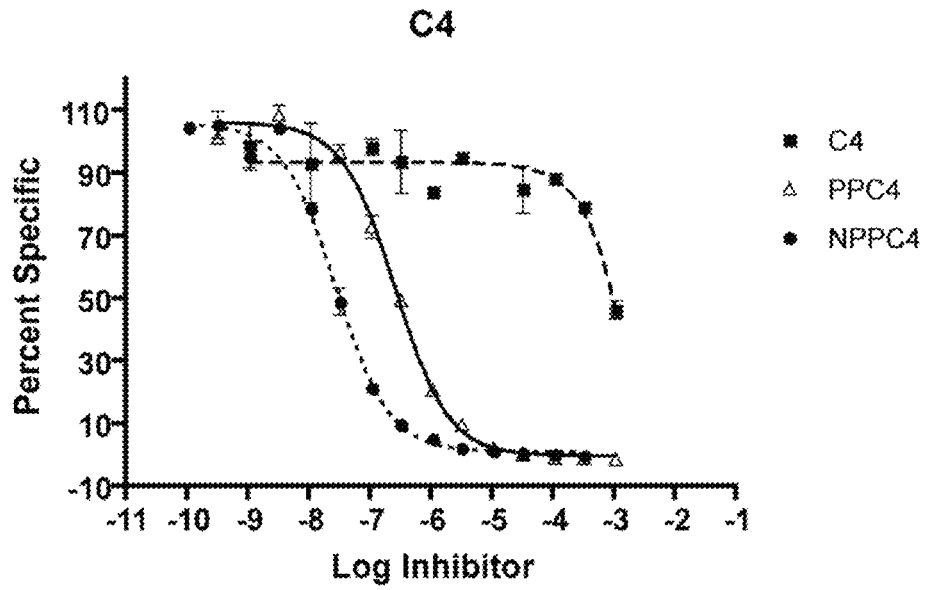
B.
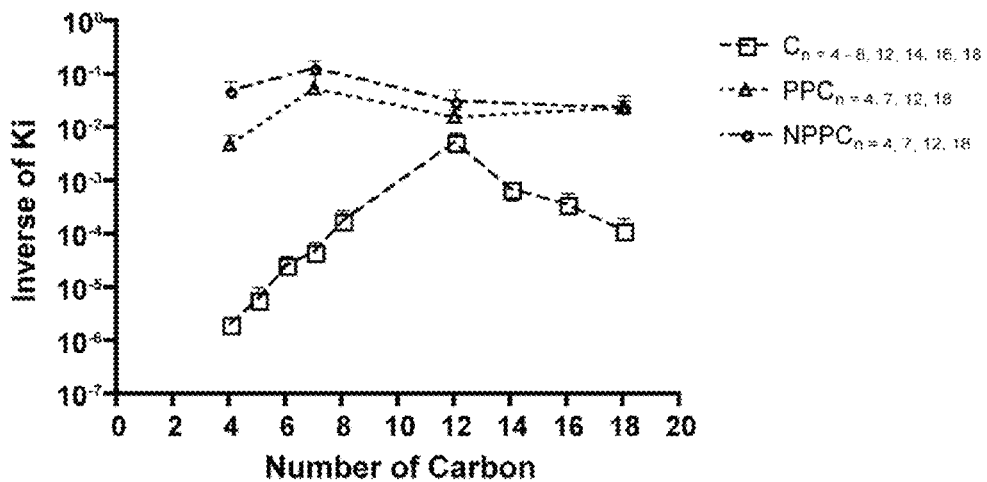
Figure 1

| Cell Line: | Compound | DPT | UC1 | UC2 | UC3 | UC4 | HA1 | HA2 | HD1 | HD2 | HD3 | HD4 | HD5 | HD6 |
|---|---|---|---|---|---|---|---|---|---|---|---|---|---|---|
| NCI-H460 | IC50 (uM) | >100 | 44.67 | 38.19 | 55.11 | 17.71 | >100 | >100 | >100 | 40.52 | 44.77 | >100 | 40.32 | >100 |
| Human | SE | | 5.01 | 3.58 | 3.32 | 1.85 | | | | 4.86 | 7.81 | | 5.61 | |
| Lung | Conf 95 upper | | 55.05 | 45.60 | 61.99 | 21.55 | | | | 50.66 | 61.12 | | 51.95 | |
| Adenocarcinoma | Conf 95 lower | | 34.29 | 30.77 | 48.22 | 13.87 | | | | 30.38 | 28.42 | | 28.70 | |
| SKOV-3 | IC50 (uM) | >100 | >100 | 72.84 | 60.07 | 16.09 | 73.12 | >100 | 56.18 | 27.85 | 20.15 | >100 | >100 | >100 |
| Human | SE | | | 7.92 | 7.47 | 1.20 | | | 6.74 | 5.13 | 5.34 | | | |
| Ovarian | Conf 95 upper | | | 89.27 | 75.57 | 18.59 | | | 70.30 | 38.56 | 31.36 | | | |
| Adenocarcinoma | Conf 95 lower | | | 56.42 | 44.58 | 13.60 | | | 42.06 | 17.15 | 8.94 | | | |
| Du145 | IC50 (uM) | >100 | 24.77 | 28.59 | 50.95 | 16.57 | >100 | >100 | >100 | 32.67 | >100 | >100 | 13.06 | >100 |
| Human | SE | | 1.45 | 1.44 | 3.58 | 0.41 | | | | 1.62 | | | 0.58 | |
| Prostate | Conf 95 upper | | 27.78 | 31.58 | 58.39 | 17.42 | | | | 36.04 | | | 14.26 | |
| Adenocarcinoma | Conf 95 lower | | 21.76 | 25.60 | 43.52 | 15.72 | | | | 29.31 | | | 11.87 | |
| MCF7 | IC50 (uM) | >100 | 20.13 | 20.80 | 49.68 | 11.71 | 82.30 | >100 | >100 | 22.36 | 41.34 | 88.10 | 16.75 | >100 |
| Human | SE | | 1.54 | 1.43 | 18.00 | 0.49 | 0.13 | | | 1.86 | 1.75 | 6.41 | 1.48 | |
| Breast | Conf 95 upper | | 23.32 | 23.76 | 145.13 | 12.73 | 2.19 | | | 26.21 | 44.97 | 101.39 | 19.81 | |
| Adenocarcinoma | Conf 95 lower | | 16.93 | 17.83 | 70.24 | 10.68 | 1.64 | | | 18.50 | 37.70 | 74.81 | 13.68 | |
| SF-268 | IC50 (uM) | >100 | 62.79 | 39.45 | 56.96 | 15.81 | >100 | >100 | >100 | >100 | >100 | >100 | 38.80 | >100 |
| Human | SE | | 1.78 | 3.16 | 14.11 | 0.55 | | | | | | | 1.62 | |
| CNS | Conf 95 upper | | 66.49 | 46.00 | 97.00 | 16.96 | | | | | | | 42.16 | |
| Adenocarcinoma | Conf 95 lower | | 59.10 | 32.91 | 38.30 | 14.66 | | | | | | | 35.44 | |
| A549 | IC50 (uM) | >100 | 83.09 | 55.09 | 87.19 | 28.70 | >100 | >100 | >100 | >100 | >100 | >100 | >100 | |
| Human | SE | | 10.59 | 5.06 | 70.75 | 1.27 | | | | | | | | |
| Lung | Conf 95 upper | | 105.05 | 65.58 | 310.38 | 31.33 | | | | | | | | |
| Adenocarcinoma | Conf 95 lower | | 61.14 | 44.60 | 16.12 | 26.07 | | | | | | | | |

*Figure 3A*

| Cell Line: | Compound | DPT | UC1 | UC2 | UC3 | UC4 | HA1 | HA2 | HD1 | HD2 | HD3 | HD4 | HD5 | HD6 |
|---|---|---|---|---|---|---|---|---|---|---|---|---|---|---|
| MB-MDA-231 Human Breast Adenocarcinoma | IC50 (uM) SE Conf 95 upper Conf 95 lower | >100 | 32.72 2.04 36.95 28.50 | 29.96 2.10 34.32 25.60 | 54.37 3.05 60.71 48.04 | 14.68 0.77 16.27 13.09 | >100 | 42.96 5.56 54.50 31.43 | >100 | 57.12 4.72 66.90 47.33 | 68.12 3.03 74.41 61.83 | >100 | 21.60 0.98 23.63 19.57 | >100 |
| HT-29 Human colorectal Adenocarcinoma | IC50 (uM) SE Conf 95 upper Conf 95 lower | >100 | 39.67 1.42 42.61 36.72 | 29.66 0.91 31.56 27.77 | 41.68 21.48 87.09 -2.24 | 13.56 0.19 13.95 13.17 | 86.03 0.09 2.12 1.75 | >100 | >100 | >100 | >100 | >100 | 36.42 1.16 38.83 34.02 | >100 |
| HCT-15 Human colorectal Adenocarcinoma | IC50 (uM) SE Conf 95 upper Conf 95 lower | >100 | 17.89 12.14 43.14 -7.37 | >100 | >100 | 24.39 290.37 626.57 -577.80 | >100 | >100 | >100 | >100 | >100 | >100 | 54.12 7.84 70.66 37.59 | >100 |
| MCF10A Human immortalized Breast | IC50 (uM) SE Conf 95 upper Conf 95 lower | >100 | 69.46 4.66 79.12 59.80 | 53.00 5.62 64.66 41.35 | 52.59 17.83 138.87 64.72 | 15.01 0.84 16.75 13.27 | >100 | >100 | >100 | >100 | >100 | >100 | 88.63 7.38 103.94 73.32 | >100 |
| H1299 Human Lung Adenocarcinoma | IC50 (uM) SE Conf 95 upper Conf 95 lower | >100 | >100 | 81.41 4.93 91.64 71.19 | 74.68 2.86 80.61 68.74 | 28.44 0.72 29.93 26.94 | >100 | >100 | >100 | >100 | >100 | >100 | 90.81 4.44 100.01 81.60 | >100 |
| H1299 Human Lung Adenocarcinoma | IC50 (uM) SE Conf 95 upper Conf 95 lower | >100 | 39.17 5.95 51.51 26.83 | 27.75 1.35 30.55 24.96 | 39.29 0.09 1.79 1.40 | 12.96 0.66 14.33 11.59 | >100 | >100 | >100 | >100 | >100 | >100 | >100 | >100 |

*Figure 3B*

|      | X    | Y | Z    | W | R¹    | R²    |
|------|------|---|------|---|-------|-------|
| 6-1  | F    | H | F    | H | butyl | butyl |
| 6-2  | F    | F | F    | F | butyl | butyl |
| 6-3  | NO₂  | H | NO₂  | H | butyl | butyl |

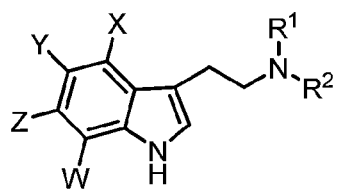

|      | X   | Y | Z   | W | R¹            | R²     |
|------|-----|---|-----|---|---------------|--------|
| 6-4  | H   | H | NO₂ | H | methyl        | methyl |
| 6-5  | NO₂ | H | NO₂ | H | methyl        | methyl |
| 6-6  | H   | H | NO₂ | H | butyl         | butyl  |
| 6-7  | NO₂ | H | NO₂ | H | butyl         | butyl  |
| 6-8  | F   | H | H   | H | methyl        | methyl |
| 6-9  | F   | F | H   | H | methyl        | methyl |
| 6-10 | F   | F | F   | H | methyl        | methyl |
| 6-11 | F   | F | F   | F | methyl        | methyl |
| 6-12 | F   | H | H   | H | butyl         | butyl  |
| 6-13 | F   | F | H   | H | butyl         | butyl  |
| 6-14 | F   | F | F   | H | butyl         | butyl  |
| 6-15 | F   | F | F   | F | butyl         | butyl  |
| 6-16 | H   | H | NO₂ | H | -(CH₂)₄-F¹⁸   | butyl  |
| 6-17 | NO₂ | H | NO₂ | H | -(CH₂)₄-F¹⁸   | butyl  |
| 6-18 | F   | H | H   | H | -(CH₂)₄-F¹⁸   | butyl  |
| 6-19 | F   | F | H   | H | -(CH₂)₄-F¹⁸   | butyl  |
| 6-20 | F   | F | F   | H | -(CH₂)₄-F¹⁸   | butyl  |
| 6-21 | F   | F | F   | F | -(CH₂)₄-F¹⁸   | butyl  |

*Figure 11*

SELECTIVE SIGMA-1 RECEPTOR LIGANDS

RELATED APPLICATIONS

This application is a continuation of U.S. patent application Ser. No. 12/621,246, filed Nov. 18, 2009, and this application claims priority under 35 U.S.C. §119(e) to U.S. Provisional Patent Application No. 61/115,641, filed Nov. 18, 2008, the specifications of which are herein incorporated by reference.

GOVERNMENT SUPPORT

This invention was made with government support under MH065503 awarded by the National Institutes of Health. The government has certain rights in the invention.

BACKGROUND OF THE INVENTION

The sigma-1 receptor is a unique non-opioid, non-PCP binding site that shares no homology with any mammalian proteins. In the brain, sigma-1 receptors are known to regulate the activity of diverse ion channels via protein-protein interactions. There is emerging evidence indicating that the activation of sigma-1 receptors promotes both neuronal differentiation and anti-apoptotic action (i.e. interferes with programmed cell death), potentially leading to cancer. Ligands for the sigma-1 receptor may constitute a new class of therapeutic drugs targeting an endoplasmic reticulum (ER) protein. Heretofore, ligands, particularly antagonists of the sigma-1 receptor have been scarce and poorly studied.

Interest in the sigma-1 receptor has increased since the recent discovery that the sigma-1 receptor may be a ligand-regulated mitochondrial membrane-associated ER chaperone, potentially leading to regulation of oxidative stress in mammalian cells, and that sigma ligands may have anti-tumorigenic activities. The sigma-1 receptor has been found to have promiscuous drug binding activity. A range of different pharmacological agents such as antipsychotics, haloperidol, $Ca^{2+}$ channel antagonists such as verapamil, antidepressants such as fluoxetine, and CNS stimulants such as cocaine and methamphetamine, all bind to the sigma-1 receptor. See Hayashi et al., *Expert Opin. Ther. Targets*, 2008. 12(1): 45-58. Because of its promiscuity in drug binding activity, the sigma-1 receptor has been implicated in many different pathophysiological conditions including psychosis, drug addiction, retinal degeneration and cancer. Accordingly, new sigma ligands are needed to provide potential therapeutic agents for the treatment of these conditions and diseases.

Sigma-1 receptors are overexpressed in numerous tumor cell lines including breast cancer, small cell and non-small cell lung carcinoma, renal carcinoma, colon carcinoma, sarcoma, brain tumors, melanoma, glioblastoma, neuroblastoma, and prostate cancer. Because of this expression pattern, sigma-1 receptor ligands have potential in both imaging and treating cancer. A study showed that a putative antagonist of the sigma-1 receptor, rimcazole, was able to inhibit cellular proliferation and induce cell death. The mechanism underlying the inhibitory effect of sigma receptor drugs on tumor cell proliferation is unclear but has been shown to involve the activation of caspases 3 and 7 in the apoptotic pathway. Accordingly, the development of selective and/or high affinity sigma-1 receptor ligands is needed for diagnostic and therapeutic agent evaluation and development.

SUMMARY

The invention provides new therapeutic compounds that modulate the mammalian sigma-1 receptor. The compounds can be high affinity inhibitors of the sigma 1 receptor. These compounds have been shown to be cytotoxic against a number of cancer cell lines, including breast, lung, prostate, ovarian, colorectal and CNS. The compounds are therefore useful to provide new therapies for treating cancer, as well as for treating neurological disorders and cardiovascular disorders. Administration of an effective amount of a compound described herein can provide neuroprotective action to a mammal, such as the reduction, treatment, or elimination of cocaine addition or toxicity. The compounds can also be used as antipsychotic agents or to treat cardiovascular disorders.

Accordingly, the invention provides compounds of formula I:

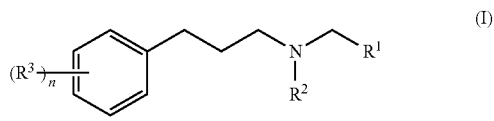
(I)

wherein $R^1$ is $(C_1-C_{13})$alkyl, aryl, or benzyl;

$R^2$ is H or $(C_1-C_{14})$alkyl;

each $R^3$ is independently H, halo, nitro, cyano, azido, amino, or carboxy;

n is 1, 2, 3, 4, or 5; and the aryl or benzyl of $R^1$ is optionally substituted with 1-5 halo, hydroxy, nitro, amino, azido, alkyl, alkoxy, trifluoromethyl, or trifluoromethoxy groups, or a combination thereof; or a salt thereof. In some embodiments, one, two, three, four, or five $R^3$ groups may substitute the illustrated phenyl group of formula I.

In certain embodiments, $R^1$ is $(C_3-C_{13})$alkyl. In other embodiments, $R^1$ is aryl substituted with one or two halo, amino, azido, alkyl, or trifluoromethyl groups. In yet other embodiments, $R^1$ is benzyl substituted with one or two halo, amino, azido, alkyl, or trifluoromethyl groups. In some embodiments, when $R^1$ is benzyl, the phenyl group of the benzyl is substituted with at least one substituent, and/or at least one $R^3$ is not hydrogen.

In certain embodiments, $R^2$ is H. In other embodiments, $R^2$ is $(C_1-C_4)$alkyl.

In certain embodiments, at least one $R^3$ is F or $NO_2$.

In some embodiments, n is one and $R^3$ is in the para position of the ring to which it is attached. In some embodiments, n is two, three, four, or five. The $R^3$ substituents can be in any combination of ortho, meta, and/or para, with respect to the phenyl ring's propyl amine group in formula I.

In certain specific embodiments, the compound of formula I is

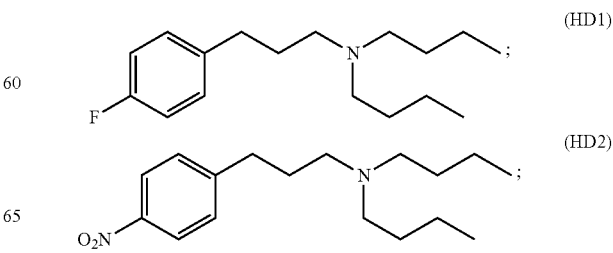

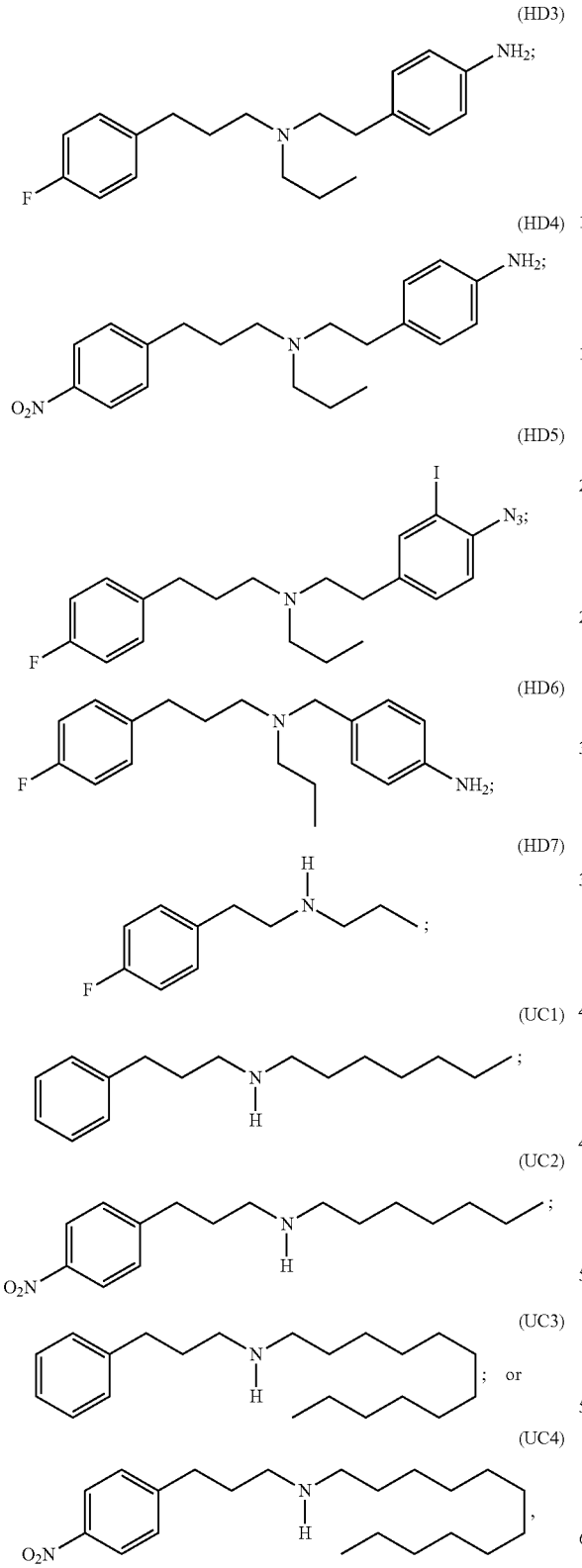

or a salt thereof.

Accordingly, in some embodiments, for example for HD7, the phenyl propyl group shown in formula I can be a phenyl ethyl group (i.e., one of the methylene groups shown is absent). The invention further provides compositions comprising a compound of formula I and a pharmaceutically acceptable diluent or carrier.

Also provided is a method of modulating a sigma-1 receptor in a mammal comprising administering to the mammal an effective amount of a compound formula I. The modulating can be agonism of the sigma-1 receptor or antagonism of the sigma-1 receptor. Such activity can be used to treat drug addiction, such as opiate addition or cocaine addiction.

The invention also provides a method of inhibiting cancer cell growth comprising contacting the cell with an effective inhibitory amount of a compound formula I, so as to inhibit the growth of the cancer cells, inhibit replication of the cancer cells, and/or in some embodiments, kill the cancer cells. The cancer cell can be, for example, a breast cancer cell, lung cancer cell, prostate cancer cell, ovarian cancer cell, colorectal cancer cell, or a CNS cancer cell.

The invention further provides methods for stabilizing a sigma-1 receptor such that the sigma-1 receptor substantially maintains its native structure during extraction from a membrane, during isolation, and/or during crystallization. Accordingly, a compound described herein can be used to aid protein crystallization by contacting the protein with the compound to stabilize the protein, followed by extraction and/or isolation, followed by protein crystallization, for example, in the presence of protein surfactants.

The compounds and compositions can also be used to prepare or manufacture a medicament useful to treat a disease or condition in a mammal, for example, cancer, or another condition modulated by a sigma-1 receptor, in a human. Also provided are useful intermediates for the preparation of the compounds and compositions disclosed herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 1. A. Inhibition of [$^3$H]-(+) pentazocine binding to the *E. coli* expressed and purified sigma-1 receptor by butylamine (C4) and its N-3-phenylpropyl (PPC4) and N-3-(4-nitrophenylpropyl) (NPPC4) derivatives. B. A plot showing the relation of the Ki values of amines and amine derivatives to the carbon chain length.

FIGS. 3. A and B. Inhibition of tumor cell lines by compounds of the invention, according to various embodiments of the invention.

FIG. 11. Compounds 4-21; examples of compounds that include one to four $R^3$ groups, according to an embodiment. The $R^1$ and $R^2$ groups can each be, for example, any ($C_1$-$C_{14}$) alkyl, optionally terminated with an F or $^{18}$F group. Groups X, Y, Z, and W can each independently be any halo or nitro group.

DETAILED DESCRIPTION

Figure 2:
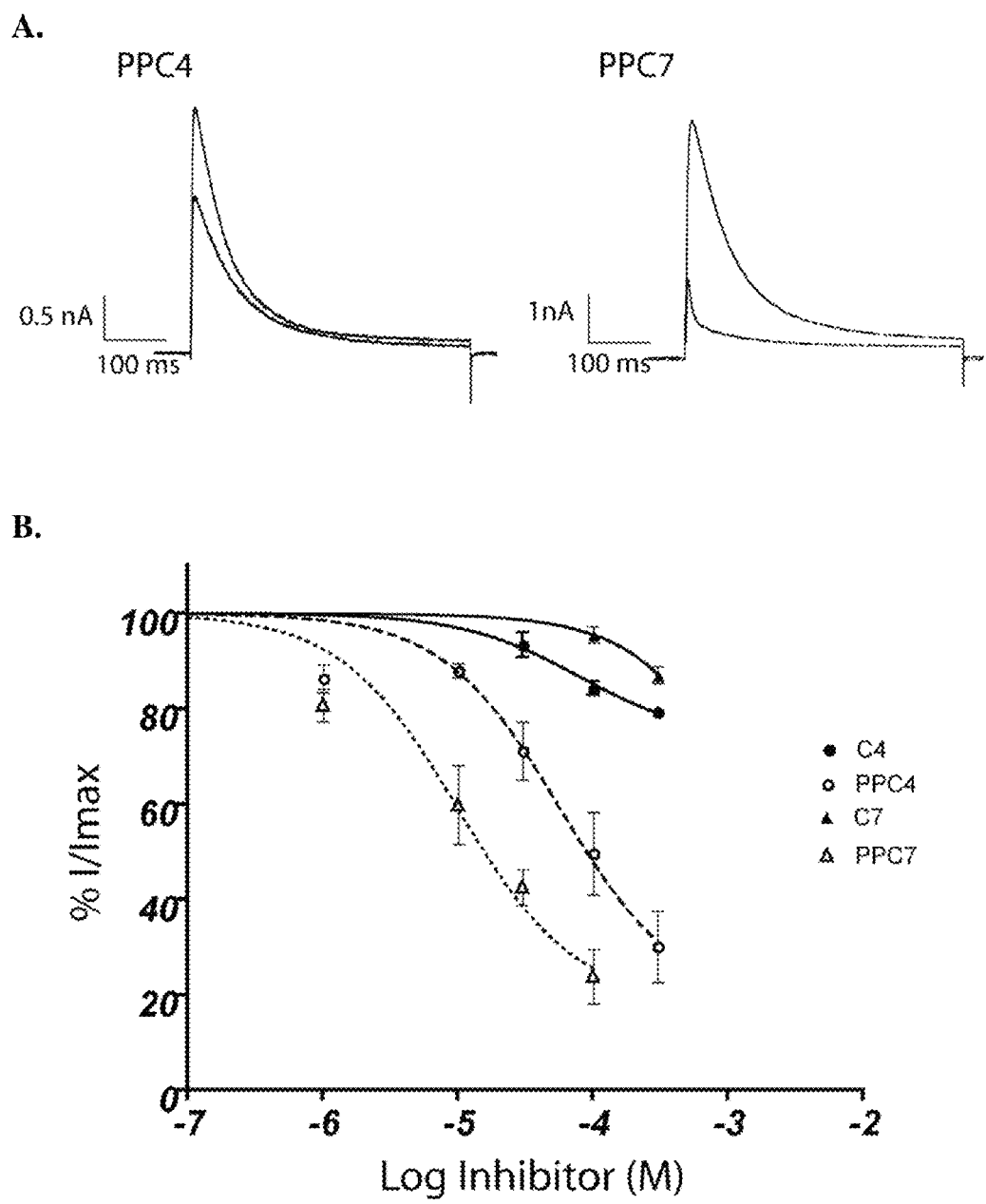
FIG. 2. A. Representative K$^+$ channel current traces showing inhibition of K$_v$1.4 K$^+$ channel expressed in HEK-293 cells by phenylpropyl derivatives of N-alkylamines. K$^+$ channels were activated by 400 ms pulses to +20 mV from a resting potential of −80 mV. B. Concentration response curves of butylamine, heptylamine and the corresponding phenylpropyl and nitrophenylpropyl compounds. The leftward shift of the response curve for the N-3-phenylpropyl derivatives corresponds with the increase in affinity at the sigma-1 receptor.

The sigma-1 receptor cloned from various sources encodes a protein of 25.3 kDa with greater than 95% sequence similarity across different species. A sigma-2 receptor has been identified based on ligand binding and photolabeling studies but is yet to be cloned. Through the use of radioiodinated sigma-1 receptor ligands and cross-linking reagents, it has been have shown that steroid-binding domain like I (SBDLI) and SBDLII are in close proximity and form the binding regions for sigma-1 receptor ligands. Using various synthetic compounds, the pharmacophore for high sigma-1 receptor ligands have been defined to include N,N-dialkylated phenylpropyl amine, such as an N,N-dimethylated phenylpropyl amine.

Work by Glennon et al. (*Mini Rev. Med. Chem.*, 2005. 5(10): 927-40) and various molecular modeling studies have identified pharmacophores significantly different than the N-dimethylated phenylpropyl amine moiety described herein. These studies also have paid little attention to long chain alkylamines such as tridemorph (2,6-dimethyl-4-tridecylmorpholine), which is a fungicide having affinity for the sigma-1 receptor similar to that of fenpropimorph (4-[3-(4-tert-butylphenyl)-2-methylpropyl]-2,6-dimethylmorpholine) (Moebius et al., *Br. J. Pharmacol.*, 1997. 121(1): p. 1-6), and (2R-trans)-2-butyl-5-heptylpyrrolidine, which is a compound isolated from the culture broth of *Streptomyces longispororuber* (Kumagai et al., J. Antibiot. (Tokyo), 2000. 53(5): 467-73).

For the compounds and methods described herein, characterization of the sigma-1 receptor ligand binding regions was sought by employing N-alkylamines of varying chain length and their N-3-phenylpropyl and N-3-(4-nitrophenyl)propyl derivatives. In addition, functional characterization on the modulation of Kv 1.4 K$^+$ channels was performed. The characterization provided significant data that defined the pharmacophore features of high affinity ligands at the sigma-1 receptor.

Tridemorph, a $C_8$-$C_7$ sterol isomerase inhibitor and a potent sigma-1 receptor ligand, is structurally different from most known sigma-1 receptor ligands because it contains an aliphatic 13 carbon alkyl chain. Using N-alkylamines with varying carbon chain length, the sigma-1 receptor binding regions for these compounds were explored in order to discover a more potent and selective sigma-1 receptor ligand. It was found that dodecylamine has the highest affinity among N-alkylamines from butyl to octadecylamines. N-3-Phenylpropyl and N-3-(4-nitrophenyl)propyl substitutions to the nitrogen both enhanced the affinities of these compounds at the sigma-1 receptor site and correlate with the their potencies at the Kv 1.4 K$^+$ channel assay.

A series of compounds that have high affinity for the sigma-1 receptor are described herein. Cytotoxicity assays indicate that the synthesized compounds are cytotoxic against a number of cancer cells lines including breast, lung, prostate, ovarian, colorectal, and CNS, indicating their utility as anticancer agents. The compounds may induce apoptosis and it was discovered that certain sigma-1 receptor ligands used in the cytotoxicity assays showed that some cancer cell lines are more susceptible than others, potentially due to the expression pattern of the sigma-1 receptor in these cell lines.

Regulated changes in intracellular reactive oxygen species (ROS) levels can induce biochemical signaling processes that control basic cellular functions, such as proliferation and apoptosis, which are prevalent in cancer development. Data indicate that the sigma-1 receptor may have a function in suppressing the formation of ROS because the sigma-1 receptor knock-out (KO) mouse showed elevated ROS. Accordingly, ROS may be involved in sigma ligand mediated cell death.

Through the use of radioiodinated, known sigma-1 receptor ligands and cross-linking reagents, the steroid-binding domain like I (SBDLI) and SBDLII regions were found to be in close proximity. Together they form the binding regions for sigma-1 receptor ligands. Using various synthetic compounds, a pharmacophore for high affinity sigma-1 receptor ligands has been defined. Work by others dating back as far as 20 years identified a different pharmacophore. Those earlier studies did not include certain important features described herein for the binding affinity and inhibition of the sigma-1 receptor activity, such as a long chain alkylamine and/or electron withdrawing groups. The long chain alkylamine moiety can be optionally substituted as described herein. Electron withdrawing groups on the phenyl of the phenylpropyl amine can also enhance the compounds affinity for the sigma-1 receptor.

The sigma-1 receptor ligand binding regions have been characterized herein using N-alkylamines of varying chain length and their corresponding N-3-phenylpropyl and N-3-(4-nitrophenyl)propyl derivatives. In addition, functional characterization on the modulation of potassium ion channels was performed. These data provide important parameters of pharmacophore features of high affinity ligands of the sigma-1 receptor. These features define important elements of the molecular scaffold.

Definitions

As used herein, certain terms have the following meanings. All other terms and phrases used in this specification have their ordinary meanings, as one of skill in the art would understand. Such ordinary meanings may be obtained by reference to technical dictionaries, such as *Hawley's Condensed Chemical Dictionary*, 14$^{th}$ Edition, by R. J. Lewis, John Wiley & Sons, New York, N.Y., 2001.

References in the specification to "one embodiment", "an embodiment", etc., indicate that the embodiment described may include a particular feature, structure, or characteristic, but every embodiment may not necessarily include that particular feature, structure, or characteristic. Moreover, such phrases are not necessarily referring to the same embodiment. Further, while a particular feature, structure, or characteristic may be described in connection with one embodiment, such feature, structure, or characteristic may also be used or excluded in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of ±5%, 10%, or 20% of the value specified. For example, "about 50" percent can in some embodiments carry a variation from 45 to 55 percent. For integer ranges, the term "about" can include one or two integers greater than and/or less than a recited integer.

Specific values listed below for radicals, substituents, and ranges, are for illustration only; they do not exclude other defined values or other values within defined ranges for radicals and substituents in some embodiments, but they may be excluded from other embodiments.

The term "alkyl" refers to a branched, unbranched, or cyclic hydrocarbon having, for example, from 1-20 carbon atoms, and often 1-14, 1-13, 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, tetradecyl, hexadecyl, octadecyl, and the like. The alkyl can be optionally partially or fully unsaturated at any suitable point along their carbon chain. As such, the recitation of an alkyl group can include both alkenyl and/or alkynyl groups. The alkyl can be a monovalent hydrocarbon radical, as described and exemplified above, or it can be a divalent hydrocarbon radical (i.e., an alkylene). In some embodiments, the alkyl group is not branched or cyclic, and/or the alkyl group is fully saturated. Any specific carbon length can also be excluded from a range of possible values for the alkyl group.

The term "aryl" refers to an unsaturated aromatic carbocyclic group of from 6 to 14 carbon atoms having a single ring (e.g., phenyl) or multiple condensed (fused) rings, wherein at least one ring is aromatic (e.g., naphthyl, dihydrophenanthrenyl, fluorenyl, or anthryl). The aryl can be unsubstituted or substituted.

The term "halo" refers to fluoro, chloro, bromo, and iodo. Similarly, the term "halogen" refers to fluorine, chlorine, bromine, and iodine. The term halo can include isotopes of halo atoms, such as $^{18}$F and $^{125}$I.

The terms "treat" and "treatment" refer to any process, action, application, therapy, or the like, wherein a mammal, including a human, is subject to medical aid with the object of improving the mammal's condition, either directly or indirectly. Treatment typically refers to the administration of an effective amount of a compound or composition described herein.

The terms "effective amount" or "therapeutically effective amount" are intended to qualify the amount of a therapeutic agent required to relieve to some extent one or more of the symptoms of a condition, disease or disorder, including, but not limited to: 1) reduction in the number of cancer cells; 2) reduction in tumor size; 3) inhibition of (i.e., slowing to some extent, preferably stopping) cancer cell infiltration into peripheral organs; 4) inhibition of (i.e., slowing to some extent, preferably stopping) tumor metastasis; 5) inhibition, to at least some extent, of tumor growth; 6) relieving or reducing to some extent one or more of the symptoms associated with a condition or disorder; and/or 7) relieving or reducing the side effects associated with the administration of active agents.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, can be referred to as prevention, chemoprevention, or cure. The inhibition can be about 10%, about 25%, about 50%, about 75%, or about 90% inhibition, with respect to progression that would occur in the absence of treatment. Other amounts of inhibition are illustrated or recited in the Examples and Figures herein.

As used herein, "contacting" refers to the act of touching, making contact, or of bringing to immediate or close proximity, including at the cellular or molecular level.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

Reference to compounds described herein can include the compounds as their corresponding salts forms. Examples of salts of the compounds include salts derived from an appropriate base, such as an alkali metal (for example, sodium), an alkaline earth (for example, magnesium), ammonium, or $NX_4^+$ (wherein each X is independently H or $C_1$-$C_4$ alkyl). Salts of an amino group include salts of organic carboxylic acids such as acetic, benzoic, lactic, fumaric, tartaric, maleic, malonic, malic, isethionic, lactobionic or succinic acids; organic sulfonic acids, such as methanesulfonic, ethanesulfonic, benzenesulfonic or p-toluenesulfonic acids; or inorganic acids, such as hydrochloric, sulfuric, phosphoric or sulfamic acids. Salts of a compound of a hydroxy group include the anion of said compound in combination with a suitable cation such as $Na^+$ and $NX_4^+$ (wherein each X is independently H or a $C_1$-$C_4$ alkyl group).

The terms "diluent" and "carrier" refer to typically inert substances used to reduce the concentration of a particular agent in a given volume. A liquid carrier or vehicle can be a solvent or liquid dispersion medium comprising, for example, water, normal saline, ethanol, a polyol (for example, glycerol, propylene glycol, liquid polyethylene glycols, and the like), vegetable oils, nontoxic glyceryl esters, and suitable mixtures thereof. Compositions of a compound and a pharmaceutically acceptable carrier can also include an appropriate buffer and/or salt.

Compounds of the Invention:

The compounds of the invention include compounds of formula I:

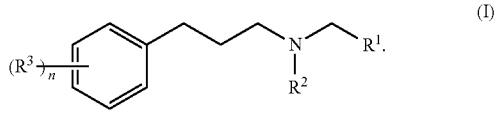

(I)

$R^1$ can be $(C_1$-$C_{13})$alkyl, aryl, or benzyl. The $(C_1$-$C_{13})$alkyl group can be a straight or branched chain of 1, 2, 3, 4, 5, 6, 7, 8, 9, 10, 12, or 13 carbons, or a range of any two of the aforementioned integers. The aryl or benzyl groups can be optionally substituted, for example, with 1, 2, 3, 4, or 5 halo, amino, azido, alkyl, or trifluoromethyl groups, or any combination thereof. The substituents can be ortho, meta, or para, or a combination thereof, with respect to the attachment point of the aryl or benzyl group to the remainder of formula I.

In some embodiments, $R^1$ is not aryl, and/or $R^1$ is not benzyl. In some embodiments, $R^3$ is not H and/or the aryl group of $R^1$ is substituted with at least one substituent. In some embodiments, $R^3$ is substituted with at least one substituent.

$R^2$ can be H or $(C_1$-$C_{14})$alkyl. Similar to $(C_1$-$C_{13})$alkyl, $(C_1$-$C_{14})$alkyl can be an optionally substituted straight or branched chain of 1, 2, 3, 4, 5, 6, 7, 8, 9, 10, 12, 13, or 14 carbons, or a range of any two of the aforementioned integers. Any of the aforementioned integers can also be excluded from an embodiment for $R^1$ and/or $R^2$.

The variable n can be 1, 2, 3, 4, or 5.

$R^3$ can be H, halo, nitro, cyano, azido, amino, or carboxy. In one embodiment, $R^3$ can be an electron withdrawing group, as the term is understood by one skilled in the art. Each $R^3$ group can be the same, different, or a combination thereof. In some embodiments, a value for $R^3$ is excluded as a substituent of the compound.

In various embodiments, $R^3$ can be in the ortho, meta, or para position of the ring to which it is attached, with respect to the propyl amine group of formula I. When n is more than one, the $R^3$ groups can be any combination of ortho, meta, and para.

The compound of formula I can also be a compound of formula II:

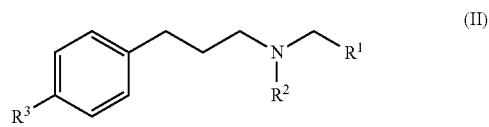

(II)

wherein $R^1$, $R^2$, and $R^3$ are as defined for formula I.

In certain embodiments, $R^1$ can be $(C_3$-$C_{13})$alkyl. In other embodiments, $R^1$ can be aryl substituted with one or two halo, amino, azido, alkyl, or trifluoromethyl groups. In yet other embodiments, $R^1$ can be benzyl substituted with one or two halo, amino, azido, alkyl, or trifluoromethyl groups.

In certain embodiments, $R^2$ is H. In other embodiments, $R^2$ is $(C_1$-$C_4)$alkyl, $(C_2$-$C_4)$alkyl, $(C_3$-$C_4)$alkyl, methyl, ethyl, propyl, or butyl.

In certain embodiments, $R^3$ is F or $NO_2$. In other embodiments, $R^3$ is not H.

The compounds of formula I and II may also be present in salt forms, for example, HCl salts.

Compound Administration

Compounds can be suitably formulated into pharmaceutical compositions for administration to human subjects in a biologically compatible form suitable for administration in vivo. Accordingly, in certain embodiments, a pharmaceutical composition is provided that includes compounds as described herein, admixed with a suitable diluent or carrier. Suitable diluents or carriers include saline or aqueous dextrose, for example, a 5% aqueous dextrose solution. Such formulations can be prepared so that they are isotonic with human fluids, such as blood, or various tissue environments. In certain embodiments, it may also be desirable to prepare hypertonic or hypotonic preparations. In other embodiments, the composition can be prepared and used for in vitro experimentation, for example, in various screens and diagnostic procedures.

The compositions containing compounds can be prepared by known methods for the preparation of pharmaceutically acceptable compositions that can be administered to subjects, such that an effective quantity of the therapeutic agent within the compounds is combined in a mixture with a pharmaceutically acceptable vehicle. Suitable vehicles are described, for example, in Remington's Pharmaceutical Sciences (2003, 20th Ed.), in The United States Pharmacopeia: The National Formulary (USP 24 NF19) published in 1999, and in the Handbook of Pharmaceutical Additives (compiled by Michael and Irene Ash, Gower Publishing Limited, Aldershot, England (1995)). On this basis, the compositions include, albeit not exclusively, solutions of the compounds in association with one or more pharmaceutically acceptable vehicles or diluents, and contained in buffered solutions with a suitable pH and iso-osmotic with the physiological fluids. In this regard, reference can be made to U.S. Pat. No. 5,843,456 (Paoletti et al.). In one embodiment, the pharmaceutical compositions can be used to enhance biodistribution and delivery of a compound of the invention.

The compounds described herein can be administered to a subject in a variety of forms depending on the route of administration selected, as is readily understood by those of skill in the art. The compounds can be administered, for example, by oral, parenteral, buccal, sublingual, nasal, rectal, patch, pump, or transdermal administration in appropriately formulated pharmaceutical compositions. Parenteral administration includes intravenous, intraperitoneal, subcutaneous, intramuscular, intrasternal, transepithelial, nasal, intrapulmonary, intrathecal, rectal and infusion modes of administration. Parenteral administration may be by continuous infusion over a selected period of time.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents can also be useful.

A compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like. A compound may also be administered parenterally.

Solutions of a compound can be prepared in water suitably mixed with suitable excipients. Under ordinary conditions of storage and use, these preparations may contain a preservative, for example, to prevent the growth of microorganisms.

The pharmaceutical forms suitable for injectable use include sterile aqueous solutions or dispersion and sterile powders for the extemporaneous preparation of sterile injectable solutions or dispersions. The formulation should be sterile and should be fluid to the extent that the solution or dispersion can be administered via syringe.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin' and glycerine. Compositions for rectal administration are conveniently in the form of suppositories containing a conventional suppository base such as cocoa butter.

The compositions described herein can be administered to an animal alone or in combination with pharmaceutically acceptable carriers, as noted above, the proportion of which is determined by the solubility and chemical nature of the compound, chosen route of administration and standard pharmaceutical practice. In an embodiment, the pharmaceutical compositions are administered in a convenient manner such as by direct application to the infected site, e.g. by injection (subcutaneous, intravenous, parenteral, etc.). In case of respiratory infections, it may be desirable to administer the compounds of the invention and compositions comprising same, through known techniques in the art, for example by inhalation. Depending on the route of administration (e.g. injection, oral, or inhalation, etc.), the pharmaceutical compositions or compounds or biologically active agents in the compounds of the invention may be coated in a material to protect the compounds or agents from the action of enzymes, acids, and other natural conditions that may inactivate certain properties of the composition or its encapsulated agent.

In addition to pharmaceutical compositions, compositions for non-pharmaceutical purposes are also included within the scope of the invention. Such non-pharmaceutical purposes may include the preparation of cosmetic formulations, or for the preparation of diagnostic or research tools. In one embodiment, the compounds can be labeled with labels known in the art, such as florescent or radio-labels, or the like.

The dosage of the compounds of the invention can vary depending on many factors such as the pharmacodynamic properties of the compound, the rate of release of the agent from the delivery composition, the mode of administration, the age, health and weight of the recipient, the nature and extent of the symptoms, the frequency of the treatment and the type of concurrent treatment, if any, and the clearance rate of the agent and/or compound in the subject to be treated.

For example, in some embodiments, a dose of a compound formulation equivalent to about 1 mg mL$^{-1}$ to about 100 mg mL$^{-1}$ can be administered to a patient. In certain other embodiments, the compound formulation includes about 2-20, about 5-15, or about 10 mg mL$^{-1}$. The specific doses of the compounds administered according to this invention to obtain therapeutic and/or prophylactic effects will, of course, be determined by the particular circumstances surrounding the case, including, for example, the compounds administered, the route of administration, the condition being treated and the individual being treated. A typical daily dose (administered in single or in divided doses) can contain a dosage level of from about 0.01 mg/kg to about 150 mg/kg of body weight of an active therapeutic agent described herein. In some embodiments, about 5-10, about 10-20, about 20-40, about 25-50, about 50-75, about 75-100, or about 100-150 150 mg/kg of body weight of a therapeutic agent are provided in a dose. In other embodiments, about 5, 10, 15, 20, 25, 30, 40, 50, 60, 70, 75, 80, 90, 100, 110, 120, 125, 140, or 150 mg/kg of body weight of a therapeutic agent are delivered in a dose. Often times, daily doses generally will be from about 0.05 mg/kg to about 20 mg/kg and ideally from about 0.1 mg/kg to about 10 mg/kg.

One of skilled in the art can determine the appropriate dosage based on the above factors. The compounds may be administered initially in a suitable dosage that may be adjusted as required, depending on the clinical response. For ex vivo treatment of cells over a short period, for example for 30 minutes to 1 hour or longer; higher doses of compounds may be used than for long term in vivo therapy.

The compounds can be used alone or in combination with other agents that treat the same and/or another condition, disease or disorder. In another embodiment, where either or both the compound or biologically active agent is labeled, one can conduct in vivo or in vitro studies for determining optimal dose ranges, drug loading concentrations and size of compounds and targeted drug delivery for a variety of diseases.

Therapy Using Compounds of the Invention

The compounds of the invention can be formulated into a pharmaceutical solution and administered to a patient. The pharmaceutical solution formulation can allow for delivery of a requisite amount of a compounds to the body within an acceptable time, for example, about 10 minutes, to about 3 hours, typically about 1 to about 2 hours, for example, about 90 minutes. The administration can be parenteral, for example, by infusion, injection, or IV, and the patient can be a mammal, for example, a human.

A disease, disorder, or condition can be treated by administering a compound of the invention, preferably in a pharmaceutical formulation. Administration of the compositions described herein can result in a reduction in the size and/or the number of cancerous growths in a patient, and/or a reduction in one or more corresponding associated symptoms. When administered in an effective amount by the methods described herein, the compositions of the invention can produce a pathologically relevant response, such as inhibition of cancer cell proliferation, reduction in the size of a cancer or tumor, prevention of further metastasis, inhibition of tumor angiogenesis, and/or death of cancerous cells. The method of treating such diseases and conditions described below includes administering a therapeutically effective amount of a composition of the invention to a patient. The method may be repeated as necessary, for example, daily, weekly, or monthly, or multiples thereof.

Conditions that can be treated include, but are not limited to, hyperproliferative diseases, including cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer; prostate cancer; pancreatic cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; and/or lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, or T-cell anaplastic large cell lymphoma. Non-cancer conditions that are characterized by sigma-1 receptor modulation can also be treated using the methods described herein.

Using a pharmaceutical formulation of this invention, a compound of formula I (the "active agent") may be administered in a dose ranging from about 4 m g/m$^2$ to about 4000 mg/m$^2$, depending on the frequency of administration. In one embodiment, a dosage regimen for the active agent can be about 400-500 mg/m$^2$ weekly, or about 450 mg/m$^2$ weekly. See Banerji et al., *Proc. Am. Soc. Clin. Oncol.*, 22, 199 (2003, abstract 797). Alternatively, a dose of about 300 mg/m$^2$ to about 325 mg/m$^2$, or about 308 mg/m$^2$ weekly can be administered to the patient. See Goetz et al., *Eur. J. Cancer,* 38 (Supp. 7), S54-S55 (2002). Another dosage regimen includes twice weekly injections, with doses ranging from about 200 mg/m$^2$ to about 360 mg/m$^2$ (for example, about 200 mg/m$^2$, about 220 mg/m$^2$, about 240 mg/m$^2$, about 250 mg/m$^2$, about 260 mg/m$^2$, about 280 mg/m$^2$, about 300 mg/m$^2$, about 325 mg/m$^2$, 340 mg/m$^2$, about 350 mg/m$^2$, or about 360 mg/m$^2$, depending on the severity of the condition and health of the patient). A dosage regimen that can be used for combination treatments with another drug, such as docetaxel, can be to administer the two drugs every three weeks, with the dose of the active agent of about 500 mg/m$^2$ to about 700 mg/m$^2$, or up to about 650 mg/m$^2$ at each administration.

Mechanism of Action

Sigma-1 receptor ligands have been reported to inhibit cell growth via the induction of apoptosis, as measured by the activation of caspases 3 and 7. The compounds described herein can also activate the apoptotic pathway(s) through activation of these caspases. Apoptosis is the downstream of many cellular stress pathways including the ER stress responses such as elevation of ROS. The compounds disclosed herein can cause apoptosis through inhibition of the sigma-1 receptor resulting in elevation of ROS. Sigma-1 receptor ligands are selective for several cancer cell lines. For example, compound HD5 (described in the Examples below) is a potent cell growth inhibitor of both MB-MDA-231 and MCF7, while it shows lower inhibition in other cancer cell lines. This selectivity may be due to the differences in expression patterns of the sigma-1 receptor in each cell line.

General Preparatory Methods

N-Alkyl amines can be prepared from corresponding alkyl halides, for example, as shown below in Scheme A. Quantitative conversion can typically be achieved using an excess of the amine RNH$_2$ in the presence of heat (e.g., about 30° C. to about 110° C.). Refluxing conditions can provide improved yields for conversion of various alkyl halides to their corresponding alkylamines.

Scheme A

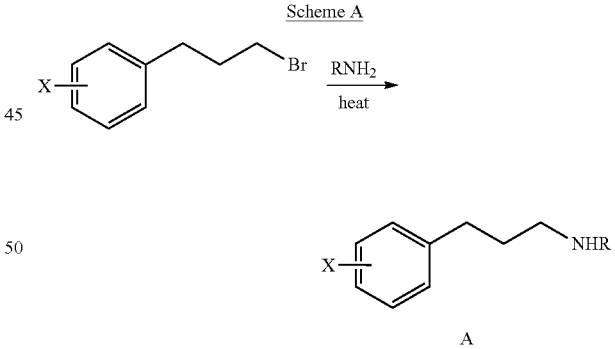

where X can be a substituent, such as H and amino, or various electron withdrawing groups such as halo, nitro, cyano, azido, or carboxy; and R can be alkyl or arylalkyl, wherein the alkyl or arylalkyl group can be optionally substituted. One to five X groups can be present on the aryl ring. The amine group of A can be further alkylated by similar procedures, or a disubstituted amine can be used to aminate the alkyl bromide starting material. Preparatory methods are further described in the Examples below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

General Materials and Methods

N-alkylamines were purchased from Acros Organics. [$^3$H]-(+)-pentazocine was purchased from Perkin Elmer Life Sciences, Wellesley, Mass. Solvents and chemicals used in syntheses were purchased from Sigma-Aldrich, St. Louis, Mo. Yields refer to isolated products after purification. Products were characterized by $^1$H, $^{13}$C NMR, mass spectroscopy, and CHN analysis.

Example 1

Preparation of N-Alkylamine Compounds

Synthesis of 1-bromo-3-(4-nitrophenyl)propane

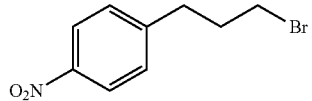

The preparation of 1-bromo-3-(4-nitrophenyl)propane from 1-bromo-3-phenylpropane (Aldrich) was carried out according to the methods of Hajipour et al. (*Tetrahedron Lett.*, 2005. 46: 8301-8310). Briefly, $P_2O_5$ and silica gel was ground at room temperature for 1 minute to homogeneity. A $P_2O_5$/silica gel mixture (1 mmol) and 1-bromo-3-phenyl-propane (1 mmol, 0.199 g) were combined and ground for 30 seconds before 0.5 mL of 65% $HNO_3$ was added. Additional grinding was carried out until TLC analysis (n-Hexane/EtOAc 9:1) showed a complete disappearance of 1-bromo-3-phenylpropane (~6 minutes). The product was extracted from the silica gel with ethyl acetate (10 mL), and was washed ($H_2O$) and dried ($MgSO_4$). Solvent was evaporated under reduced pressure and the product was purified by column chromatography (n-Hexane/EtOAc, 9:1). 1-Bromo-3-(4-nitrophenyl)propane was obtained (0.74 mmol, 0.18 g, 74%) as a yellow oil.

General Procedure for the Amination of 1-bromo-3-phenyl-propane or 1-bromo-3-(4-nitrophenyl)propane Scheme 1

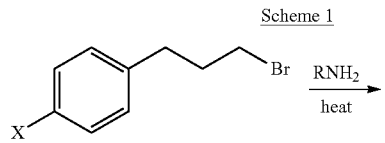

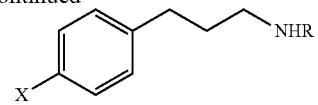

1a) X = H, R = n-Butyl
1b) X = NO$_2$, R = n-Butyl
1c) X = H, R = n-Heptyl
1d) X = NO$_2$, R = n-Heptyl
1e) X = H, R = n-Dodecyl
1f) X = NO$_2$, R = n-Dodecyl
1g) X = H, R = n-Octadecyl
1h) X = NO$_2$, R = n-Octadecyl
1i) X = NH$_2$, R = n-Octadecyl In a round bottom flask equipped with magnetic stir and condenser, two mmol of 1-bromo-3-phenyl-propane or 1-bromo-3-(4-nitrophenyl)-propane and 10 mmol of an appropriate amine (5 equiv) were refluxed in ethanol (10 mL) until TLC analysis (n-Hexane/EtOAc 90:10) showed a complete disappearance of the 1-bromo-3-phenyl-propane or 1-bromo-3-(4-nitrophenyl)-propane (~3 hours). The reaction mixture was quenched with water and extracted three times using 5 mL ethyl acetate. The combined extracts were dried using $MgSO_4$, and evaporated under reduced pressure. The purification of the product was carried out by column chromatography using silica gel and n-Hexane/EtOAc 9:1 to provide the products in 90-100% yield.

N-(3-Phenylpropyl)butan-1-amine (1a)

Yellow oil, Yields (0.30 g, 78%, 1.5 mmol). IR (KBr): 1664 cm$^{-1}$. $^1$H NMR (CDCl$_3$): δ 7.21-7.08 (m, 5H), 2.4 (m, 6H), 2.00 (m, 4H), 1.34 (m, 4H), 0.96 (t, 3H, J=7.4). $^{13}$C NMR (CDCl$_3$): δ 138.1, 128.9, 128.2, 126.1, 49.6, 49.4, 33.4, 32.8, 29.6, 20.2, 13.8. MS (CI) m/z 191 (100, M$^+$). Anal. Calcd for C$_{13}$H$_{21}$N: C, 81.62; H, 11.06; N, 7.32%. Found; C, 81.50; H, 11.20; N, 7.20%.

N-(3-(4-Nitrophenyl)propyl)butan-1-amine (1b)

Red oil, Yields (0.33 g, 70%, 1.4 mmol). IR (KBr): 1664 cm$^{-1}$. $^1$H NMR (CDCl$_3$): δ 8.21 (d, 2H), 7.55 (d, 2H), 2.4 (m, 6H), 2.00 (m, 4H), 1.34 (m, 4H), 0.96 (t, 3H, J=7.4). $^{13}$C NMR (CDCl$_3$): δ 148.1, 145.2, 130.3, 124.0, 49.6, 49.5, 32.7, 30.8, 29.5, 20.1, 13.8. MS (CI) m/z 236 (100, M$^+$). Anal. Calcd for C$_{13}$H$_{20}$N$_2$O$_2$: C, 66.07; H, 8.53; N, 11.85%. Found; C, 65.90; H, 8.70; N, 11.80%.

N-(3-Phenylpropyl)heptane-1-amine (1c)

Yellow oil, Yields (6 g, 100%, 25.7 mmol). IR (KBr): 1660 cm$^{-1}$. $^1$H NMR (CDCl$_3$): δ 7.40-7.28 (m, 5H), 2.62-2.55 (m, 6H), 1.95 (m, 3H), 1.38-1.10 (m, 10H), 0.88 (t, 3H, J=7.5). $^{13}$C NMR (CDCl$_3$): δ 148.1, 145.2, 130.3, 122.1, 49.9, 49.5, 31.8, 30.8, 30.5, 27.1, 22.6, 14.1. MS (CI) m/z 233 (100, M$^+$). Anal. Calcd for C$_{16}$H$_{27}$N: C, 82.34; H, 11.66; N, 6.00%. Found; C, 82.40; H, 11.70; N, 6.10%.

N-(3-(4-Nitrophenyl)propyl)heptane-1-amine (1d)

Red oil, Yields (0.57 g, 100%, 2 mmol). IR (KBr): 1660 cm$^{-1}$. $^1$H NMR (CDCl$_3$): δ 8.21 (d, 2H), 7.55 (d, 2H), 2.62-2.55 (m, 6H), 1.95 (m, 3H), 1.38-1.10 (m, 10H), 0.88 (t, 3H, J=7.5). $^{13}$C NMR (CDCl$_3$): δ 142.1, 128.8, 126.0, 49.9, 49.5, 31.8, 30.8, 30.5, 27.1, 22.6, 14.1. MS (CI) m/z 278 (100, M$^+$).

Anal. Calcd for $C_{16}H_{26}N_2O_2$: C, 69.03; H, 9.41; N, 10.06%. Found; C, 68.80; H, 9.60; N, 9.60%.

N-(3-Phenylpropyl)dodecan-1-amine (1e)

Oil, Yields (0.5 g, 82%, 1.6 mmol). IR (KBr): 1661 cm$^{-1}$. $^1$H NMR (CDCl$_3$): δ 7.40-7.29 (m, 5H), 2.58 (m, 6H), 1.98 (m, 3H), 1.30 (m, 20H), 0.88 (t, 3H, J=7.5). $^{13}$C NMR (CDCl$_3$): δ 142.1, 128.8, 127.6, 126.4, 49.9, 49.5, 30.7, 30.5, 29.6, 29.5, 29.3, 27.0, 22.7, 14.1. MS (CI) m/z 303 (100, M$^+$). Anal. Calcd for $C_{21}H_{37}N$: C, 83.10; H, 12.29; N, 4.61%. Found; C, 82.90; H, 12.50; N, 4.50%.

N-(3-(4-Nitrophenyl)propyl)dodecan-1-amine (1f)

Yields (0.55 g, 78%, 1.6 mmol). IR (KBr): 1660 cm$^{-1}$. $^1$H NMR (CDCl$_3$): δ 8.21 (d, 2H), 7.55 (d, 2H), 2.56 (m, 6H), 2.01 (m, 3H), 1.30 (m, 20H), 0.88 (t, 3H, J=7.5). $^{13}$C NMR (CDCl$_3$): δ 148.1, 145.2, 130.3, 124.0, 49.6, 49.5, 30.7, 30.5, 29.6, 29.5, 29.3, 27.0, 22.7, 14.1. MS (CI) m/z 348 (100, M$^+$). Anal. Calcd for $C_{21}H_{36}N_2O_2$: C, 72.37; H, 10.41; N, 8.04%. Found; C, 72.10; H, 10.50; N, 8.00%.

N-(3-Phenylpropyl)octadecan-1-amine (1g)

Yields (0.62 g, 80%, 1.6 mmol). IR (KBr): 1660 cm$^{-1}$. $^1$H NMR (CDCl$_3$): δ 7.28 (m, 5H), 2.58 (m, 6H), 2.0 (m, 3H), 1.30 (m, 32H), 0.88 (t, 3H, J=7.5). $^{13}$C NMR (CDCl$_3$): δ 142.1, 128.8, 127.6, 126.4, 49.9, 49.5, 30.7, 30.5, 29.6, 29.5, 29.3, 27.0, 22.7, 14.1. MS (CI) m/z 387 (100, M$^+$). Anal. Calcd for $C_{27}H_{49}N$: C, 83.65; H, 12.74; N, 3.61%. Found; C, 83.70; H, 12.80; N, 3.50%.

N-(3-(4-Nitrophenyl)propyl)octadecan-1-amine (1h)

Yields (0.80 g, 92%, 1.85 mmol). IR (KBr): 1660 cm$^{-1}$. $^1$H NMR (CDCl$_3$): δ 8.21 (d, 2H), 7.55 (d, 2H), 2.56 (m, 6H), 2.01 (m, 3H), 1.30 (m, 32H), 0.88 (t, 3H, J=7.5). $^{13}$C NMR (CDCl$_3$): δ 148.1, 145.2, 130.3, 124.0, 49.6, 49.5, 30.7, 30.5, 29.6, 29.5, 29.3, 27.0, 22.7, 14.1. MS (CI) m/z 432 (100, M$^+$). Anal. Calcd for $C_{27}H_{48}N_2O_2$: C, 74.95; H, 11.18; N, 6.47%. Found; C, 74.80; H, 11.40; N, 6.70%.

Example 2

Long Chain N-Alkylamines Bind to the Sigma-1-Receptor

A. Overexpression and Purification of the Sigma-1 Receptor from *E. coli*.

A guinea pig sigma-1 receptor was purified as previously described (Ramachandran et al., *Protein Expr. Purif.*, 2007. 51(2): 283-92). The pMal P2X plasmid (New England Biolabs) encoding the guinea pig sigma-1 receptor on the C-terminus of the *E. coli* Maltose Binding Protein was used for purification. The sigma-1 receptor on its C-terminus carried a hexa-histidine epitope tag. Protein was expressed in the *E. coli* strain BL21 DE3 (Novagen) with 0.6 mM IPTG. The *E. coli* pellet was sonicated and centrifuged at 100,000 g for 1 hour to separate the particulate and soluble fractions. The particulate fraction was extracted with Triton X-100, centrifuged and the extract was loaded onto an amylose resin (New England Biolabs, E-802). After washing the resin with buffer containing 0.5% Triton X-100, the MBP-sigma-1 receptor fusion protein was eluted with buffer containing 10 mM maltose.

The MBP-sigma-1-receptor fusion protein was cleaved with Factor Xa protease (Novagen) at room temperature for 24-48 hours and the cleavage was monitored with SDS-polyacrylamide gel electrophoresis. The sigma-1 receptor from the Factor Xa cleavage was purified with a HIS-Select HC Nickel affinity gel (Sigma-Aldrich P6611) in a batch format. The resin was washed with buffer containing 0.5% Triton X-100 detergent and the beads were separated by a brief centrifugation at 4000 rpm in a microcentrifuge. After washing to remove MBP, the pure sigma-1 receptor was eluted in buffer containing 250 mM imidazole.

To remove the undigested MBP-sigma-1 receptor fusion protein that is carried over in the Ni$^{2+}$ purification, the eluate from the Ni$^{2+}$ purification was incubated with Anti-MBP antibody conjugated to agarose (Vector Laboratories, Burlingame, Calif.) at 4° C. for 18-24 hours. The beads were separated by centrifugation and the supernatant contained the pure sigma-1 receptor.

B. Competitive Displacement of [$^3$H]-(+)-pentazocine

Competition ligand binding to the pure sigma-1 receptor was performed as previously described. Binding was carried out in 50 mM Tris-C1, pH 8.0 in a total volume of 100 µL containing 50-100 ng of pure sigma-1 receptor, 10 nM [$^3$H]-(+)-pentazocine and different concentration of inhibitor to be tested. After incubation at 30° C. for 60 minutes, the reaction was terminated by rapid filtration through glass fiber filters (Whatman GF/B), using a Brandel cell harvester (Brandel, Gaithersburg, Md.). The glass fiber filters were pre-soaked in 0.5% polyethyleneimine (PEI) for at least 1 hour at room temperature (~23° C.). Filters were washed 4 times with 4 mL of ice-cold 50 mM Tris-C1, pH 8.0. Radioactivity was quantified by liquid scintillation counting using a Packard model 1600 CA scintillation counter.

C. Patch Clamp Recording

A pIRES bicistronic mammalian expression plasmid (BD Biosciences, Clonetech) was constructed which carried the rat Kv 1.4 in the first multiple cloning site and rat sigma-1 receptor in the second multiple cloning site. Human Embryonic Kidney (HEK-293) were cultured on 60 mm dishes and transfected with 3 µL of Lipofectamine 2000, 2 µg of pIRES KvS1R and 0.3 µg of pEGFP (BD Biosciences, Clonetech) following manufacturers instructions. After transfection (36-48 hours), whole cell K$^+$ currents were recorded from GFP positive HEK cells under voltage clamp using standard patch clamp techniques, using patch pipettes filled with (in mM) 120 KCl, 10 NaCl, 10 EGTA, 2 MgCl$_2$, 2-4 MgATP, 0.3 NaGTP, 10 HEPES, pH 7.3.

The external solution was composed of (in mM) 130 NaCl, 4 KCl, 2 CaCl$_2$, 1 MgCl$_2$, 10 HEPES, pH 7.4 at room temperature (22-24° C.). Patch pipettes with resistances from 1-3 MΩ were fabricated from borosilicate glass (Garner Glass Co., CA). K$^+$ channels were activated by voltage step from −120 mV to 20 mV for 250 ms. Axopatch 200B, patch clamp amplifier interfaced to a PC running PCLAMP 7 (Axon Instruments) was used for data acquisition. Drugs were applied by a gravity feed system at a flow rate of 1-3 mL/minute. Series resistance compensation was used for cells with series resistance values higher than 10 MΩ. A 80-90% series resistance compensation was achieved on such cells.

Results

A. Inhibition of [$^3$H]-(+)-pentazocine binding by N-alkylamines.

Thus far, work done to define the pharmacophore of high affinity sigma-1 receptor ligands has ignored features of certain compounds, such as long chain N-alkylamine moieties, for example, those found in tridemorph and the *streptomyces*- derived compound (2R-trans)-2-butyl-5-heptylpyrrolidine. Further characterization for the ligand binding regions on the sigma-1 receptor was evaluated using N-alkylamines with varying chain length and their corresponding N-3-phenylpropyl and N-3-(4-nitrophenyl)propyl derivatives.

Butylamine to octadecylamine were tested using the competitive displacement of [$^3$H]-(+)-pentazocine binding assay at the pure sigma-1 receptor (FIG. 1A and Table 1). Aliphatic amines with 4 or more carbon atoms show measurable affinity for the pure sigma-1 receptor. The affinity increased from butylamine (Ki 477±67.5 µM) to amylamine (167±35.2 µM), hexylamine (Ki 37.5±8.7 µM), heptylamine (Ki 21.4±8.7 µM), octylamine (Ki 5.6±2.9 µM), and dodecylamine (Ki 0.18±0.02 µM). Further increase in carbon chain length did not increase the affinity compared to dodecylamine: tetradecylamine (Ki 1.4±0.03 µM), hexadecylamine (Ki 2.7±0.36 µM), and octadecylamine (Ki 8.5±5.5 µM).

TABLE 1

Radioligand Binding Data. Summary of inhibition constants of N-alkylamines binding to the purified sigma-1 receptor.

| | Ki (µM)[a] Pure σ-1R |
|---|---|
| Butylamine | 477 |
| Amylamine | 167 |
| Hexylamine | 37 |
| Heptylamine | 21 |
| Octylamine | 6 |
| Dodecylamine | 0.2 |
| Tetradecylamine | 3 |
| Hexadecylamine | 3 |
| Stearylamine | 8 |

[a]Values determined from the averages of at least 3 separate experiments; SEM was typically <25%.

Nitrogen has been reported to be an important pharmacophoric element for sigma-1 receptor binding (Ablordeppey et al., Bioorg. Med. Chem., 2000, 8(8): 2105-11). Additionally, phenylalkyl 1,2-diamines have been shown to bind to the sigma-1 receptor and have antidepressant activity (Kim et al., Methods Find. Exp. Clin. Pharmacol., 2006. 28(1): 7-11). It has been observed that N-substituted phenylpropyl and 4-nitrophenylpropyl substituents derivatized to a nitrogen atom containing alkyl or dialkyl substitution enhanced affinity for the sigma-1 receptor (Chen et al., Biochemistry, 2007, 46(11): p. 3532-42). However, the data of this Example shows that the addition of a phenylpropyl group to the nitrogen of the aliphatic amines significantly increases affinity for the sigma-1 receptor.

N-3-Phenylpropyl and N-3-(4-nitrophenyl)propyl derivatives of butyl-, heptyl-, dodecyl-, and octadecylamine were prepared. The preparation of these compounds (1a-1 h) is described above in Example 1. By testing the sigma-1 receptor binding activity by inhibition of [$^3$H]-(+)-pentazocine binding, it was demonstrated that the N-3-phenylpropyl derivatives possess 10-100 times higher affinity for the sigma-1 receptor than the compounds lacking the phenylpropyl moieties. The Ki for N-3-phenylpropyl amine derivatives ranged from 7.5±1.2 nM for N-(3-(4-nitrophenyl)propyl) heptan-1-amine (highest affinity) to 205±18.5 nM for N-(3-phenylpropyl)butan-1-amine (lowest affinity found in this series under these experimental conditions). The results from the described competitive displacement assays for N-alkylamines are summarized in Tables 1 and 2.

TABLE 2

Radioligand Binding Data. Summary of inhibition constants of N-3-phenylpropyl and N-3-(4-nitro)phenylpropyl derivatives of N-alkylamines binding to the purified sigma-1 receptor.

| | Ki (nM)[a] | | | σ-1 selectivity |
|---|---|---|---|---|
| Compound | Pure σ-1R | σ-1 Sites[b] | σ-2 Sites[c] | σ-2 Ki/σ-1 Ki |
| 1a. PPC4 | 205 | 73 | 153 | 2 |
| 1b. NitroPPC4 | 20 | 3 | 22 | 7 |
| 1c. PPC7 | 18.4 | 15 | 33 | 2 |
| 1d. NitroPPC7 | 7.5 | 10 | 11 | 1 |
| 1e. PPC12 | 63.2 | 5301 | 2104 | 0.4 |
| 1f. NitroPPC12 | 31.8 | 5171 | 2376 | 0.4 |
| 1g. PPC18 | 42.2 | 34436 | 19923 | 0.7 |
| 1h. NitroPPC18 | 41.5 | 26900 | 8826 | 0.3 |

[a] Values were determined from the averages of at least three separate experiments; SEM was typically <25%.
[b] σ-1 Sites were determined using guinea pig liver membranes.
[c] σ-2 Sites were determined using rat liver membranes.

FIG. 1B depicts the relationship between increasing chain length (plotted on the abscissa) and the inverse of Ki of N-alkylamines and their derivatives (plotted on the ordinate). The change in affinity upon addition of N-3-phenylpropyl- and N-3-(4-nitrophenyl)propyl-derivatives is most dramatic with the shorter N-alkylamines (e.g., butylamine) and less dramatic with dodecylamine. The influence of the N-3-phenylpropyl- or N-3-(4-nitrophenyl)propyl-moiety on the affinities of these compounds for the sigma-1 receptor is less on longer chain N-alkylamines under these experimental conditions. These data support the finding that N-(3-phenylpropyl)- and N-(3-(4-nitrophenyl)propyl)-substitution to N-alkylamine chains contribute to strong binding interactions with the sigma-1 receptor.

B. N-3-phenylpropyl Amines Inhibit the Kv 1.4 K$^+$ Channel Currents.

The sigma-1 receptor has been shown to modulate the activity of ion channels such as K$^+$, Ca$^{2+}$, and Cl$^-$ channels. To evaluate the functional property of N-3-phenylpropyl derivatives on a known effector of the sigma-1 receptor, Kv 1.4 and sigma-1 receptor were co-expressed in human embryonic kidney (HEK-293) cells. Coexpression of both Kv 1.4 and sigma-1 receptor was achieved by the use of a pIRES vector (Clonetech) that carried both the Kv 1.4 and sigma-1 receptor sequences. K$^+$ currents were recorded using whole cell patch clamp technique. Butylamine and heptylamine at concentrations up to 300 µM did not significantly inhibit the Kv 1.4 K$^+$ channel with average inhibition being 21% for butylamine and 15% heptylamine. However, the N-3-phenylpropyl derivatives of the butylamine and heptylamine showed profound inhibition of the Kv 1.4 K$^+$ channel at the same concentrations. The EC$_{50}$ for inhibition of the Kv 1.4 K$^+$ channel was 50 µM for N-(3-phenylpropyl)butan-1-amine and 10 µM for N-(3-phenylpropyl)heptan-1-amine. This dramatic increase in the potency of the N-3-phenylpropyl derivatives to inhibit the Kv 1.4 K$^+$ channel corresponds with the increase in affinity for the sigma-1 receptor.

SUMMARY

A series of alkyl amines were evaluated for their affinity at the sigma-1 receptor. The length of the carbon chain was found to have an effect on the affinity of alkyl amines at the sigma-1 receptor, with the twelve carbon, dodecylamine, having maximum affinity for the specific structures tested. The addition of a hydrophobic group connected by an alkyl chain, such as a propyl, to the nitrogen of the N-alkylamines, and nitro substitution at the para position of the phenyl ring, enhanced affinity of sigma-1 receptor ligands.

N-phenylpropyl derivatives of N-alkylamine were approximately 100-1000 fold higher affinity for the sigma-1 receptor than the corresponding amines. Nitro derivatives showed an even higher affinity than the corresponding phenylpropyl derivatives. However, nitro substitution on the phenyl ring of N-(3-phenylpropyl)octadecan-1-amine did not enhance further affinity, suggesting that this substitution plays a lesser role in longer chain N-alkylamines. The sigma-1 receptor has been shown to interact with the Kv 1.4 $K^+$ channel and sigma ligands were shown to inhibit channel currents. In correlation with the binding data, N-3-phenylpropyl and N-3-(4-nitrophenylpropyl)-substitution to the nitrogen are also more potent at inhibiting channel currents.

A pharmacophore for high affinity sigma-1 receptor ligands proposed by Glennon and coworkers included two hydrophobic regions flanking a central nitrogen atom. The primary hydrophobic region is situated such that a 5-(phenyl)pentyl or 5-(cyclohexyl)pentyl moiety is accommodated. The secondary hydrophobic site is smaller than the primary site and optimally accommodates a three-atom chain. The N-3-phenylpropyl- and N-3-(4-nitrophenyl)propyl-moieties of N-alkylamine derivatives described herein can readily occupy the primary hydrophobic region. However, the long carbon chain region of the N-alkylamine derivatives must be interacting with the secondary hydrophobic site on the Glennon proposed pharmacophore. It has never been reported that this secondary hydrophobic region can accommodate compounds with such a long carbon chain as dodecylamine. The binding of such molecules to the sigma-1 receptor indicate that the current pharmacophore for high affinity sigma-1 receptor ligand should be modified to include long chain alkylamines regions as described herein.

Example 3

Alkylamine Derivatives as Sigma-1 Modulators

Table 3 illustrates compounds according to various embodiments of the invention, and their affinity for the sigma-1 receptor. In some embodiments, the compounds can be sigma-1 agonists, and in other embodiments, the compounds can be sigma-1 antagonists.

TABLE 3

| Ligand | Structure | Sigma-1 $K_D$ (nM) |
|---|---|---|
| HD1 | 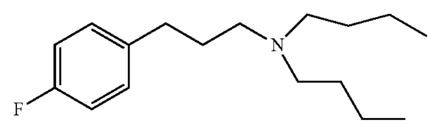 [SMILES: CCCCN(CCCC)CCCc1ccc(F)cc1] | 17.7 |
| HD2 | 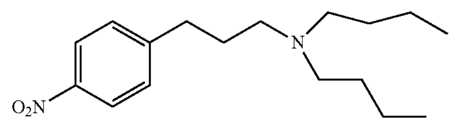 [SMILES: CCCCN(CCCC)CCCc1ccc([N+](=O)[O-])cc1] | 0.36 |
| HD3 | 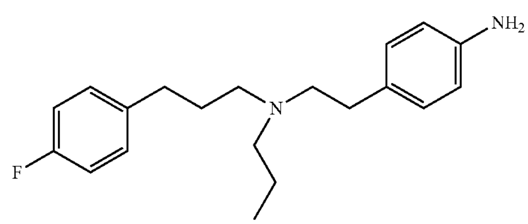 [SMILES: CCCN(CCCc1ccc(F)cc1)CCc1ccc(N)cc1] | 2590 |
| HD4 | 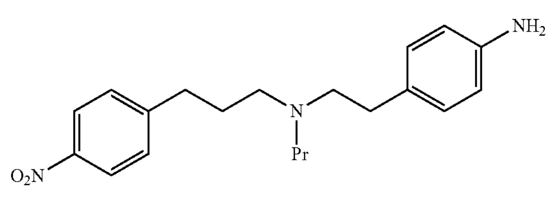 | 6 |
| HD5 | 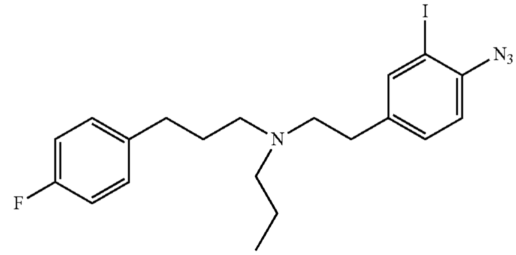 [SMILES: CCCN(CCCc1ccc(F)cc1)CCc1ccc(N=[N+]=[N-])c(I)c1] | 7239 |

TABLE 3-continued

| Ligand | Structure | Sigma-1 $K_D$ (nM) |
|---|---|---|
| HD6 | 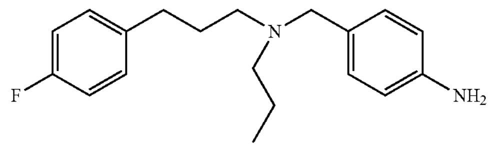 [SMILES: CCCN(CCCc1ccc(F)cc1)Cc1ccc(N)cc1] | 164 |
| HD7 | 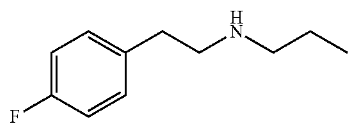 | 91 |
| UC1 | 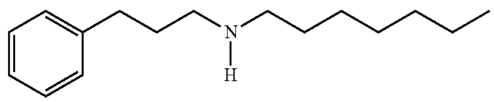 [SMILES: CCCCCCCNCCCc1ccccc1] | 12 |
| UC2 | 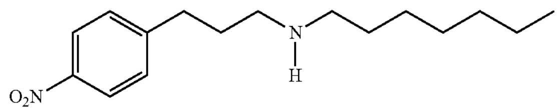 [SMILES: CCCCCCCNCCCc1ccc([N+](=O)[O-])cc1] | 5.7 |
| UC3 | 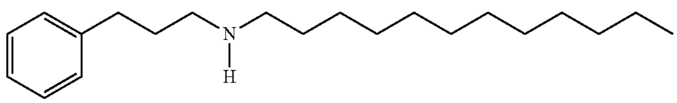 [SMILES: CCCCCCCCCCCCNCCCc1ccccc1] | 92 |
| UC4 | 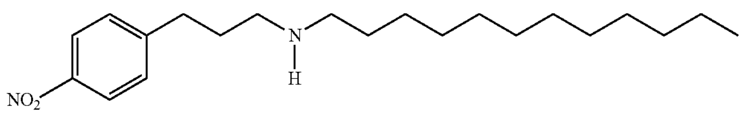 [SMILES: CCCCCCCCCCCCNCCCc1ccc([N+](=O)[O-])cc1] | 0.39 |
| DMT | 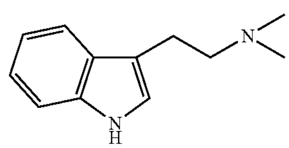 | 14600 |
| DPT | 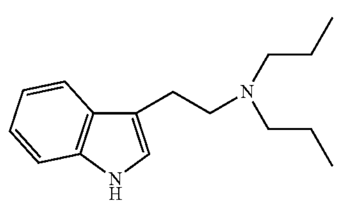 [SMILES: CCCN(CCC)CCc1c[nH]c2ccccc12] | 1600 |

Figure 4:
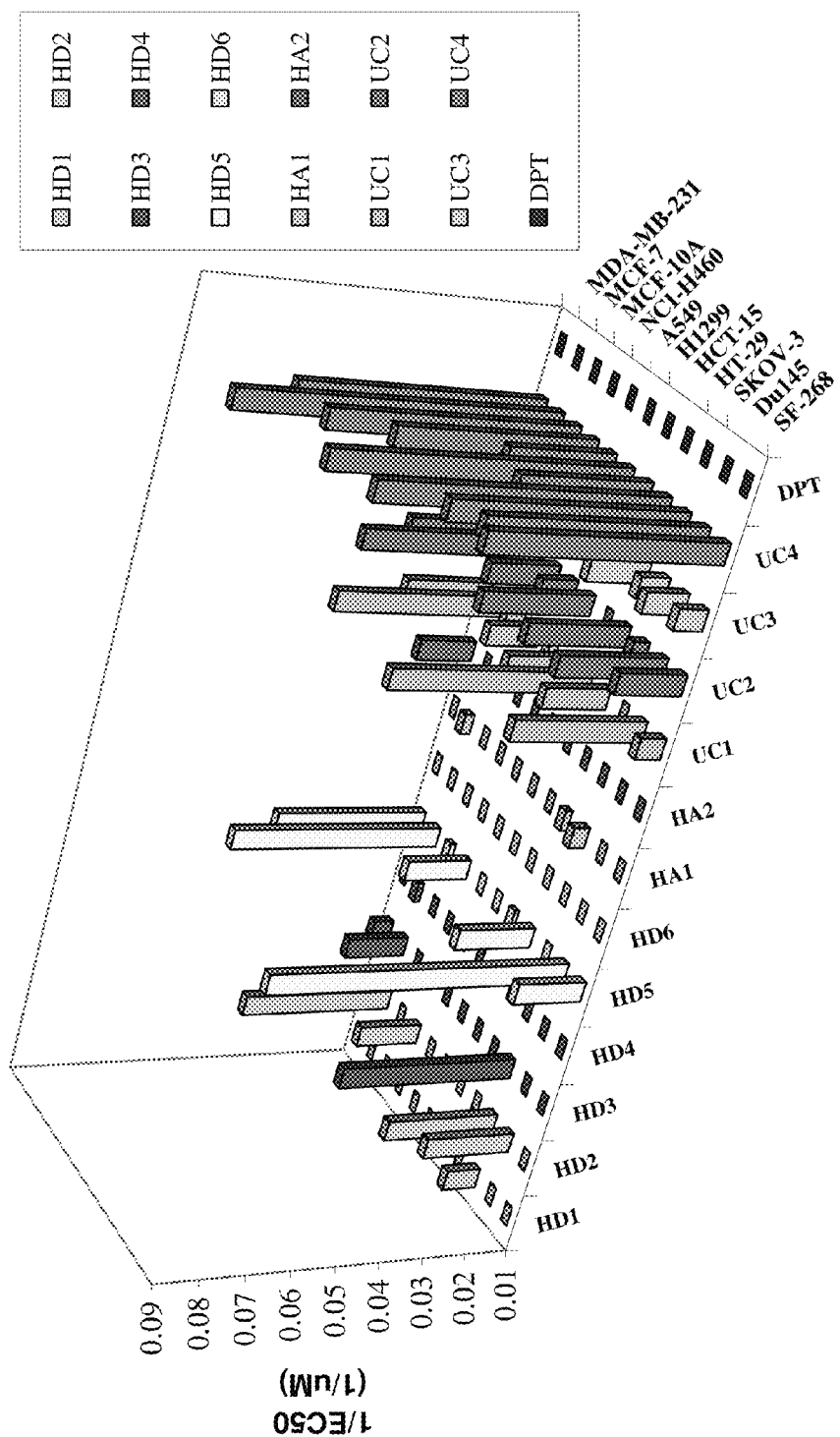
FIG. 4. Graphical illustration of $1/EC_{50}$ of various compounds of the invention plotted against various tumor cell lines.

These compounds show inhibitory properties and high selectivity against several cancer cell lines, as illustrated in FIGS. 3 and 4. For example, nitrophenylpropyl-N-hepy-lamine (UC2) and nitrophenylpropyl-N-dodecylamine (UC4) show remarkable activity for inhibiting tumor growth. Therefore, a number of high affinity sigma-1 receptor ligands have been developed that are shown to be cytotoxic and/or selective against a number of cancer cells lines including breast, lung, prostate, ovarian, colorectal, and CNS adenocarcinoma cells, for example, the cell lines recited in FIGS. 3 and 4. These results demonstrate that these compounds can be used as anti-cancer agents, as well as diagnostic agents, and agents for inhibiting cancer cell growth, either in vivo, or in vitro.

Example 4

Photo-Crosslinking Reveals Unique Features of the Sigma-1 Receptor Ligand Binding Region(s)

The sigma-1 receptor has been associated with several CNS conditions such as psychosis, depression, and drug addiction through unknown mechanism(s). Recent data indicates that the sigma-1 receptor may function as a chaperone protein by forming a complex with BiP/GRP78 in the mitochondrial ER-associated membrane (MAM). Ruoho and coworkers have shown that Iodo-azido-Cocaine binds to the steroid binding domain like (SBDL) II while Iodo-azido-Fenpropimorph binds to both SBDLI and SBDLII. Additionally, using a sulfhydryl-reactive, cleavable, radioiodinated photo-cros slinking reagent, S-[[4-(4-amino-3-[(125)I]iodo-benzoyl phenyl]methyl]ester ([125)I]IABM), it has been shown that the SBDLI and SBDLII regions are juxtaposed within approximately 8 Å of each other.

Additionally, endogenous sphingolipids, including sphingosine and sphinganine, interact with the sigma-1 receptor, therefore the interaction of these lipid-like molecules with the receptor was studied using a series of N-alkylamines. N-alkylamines from butyl- to octadecylamine exhibited micromolar binding activities at the sigma-1 receptor. Dodecylamine had the highest affinity. Addition of N-(3-phenylpropyl)- and N-(3-(4-nitrophenyl)propyl)-moieties to the amino group of an N-alkylamine increased the affinity of these compounds for the sigma-1 receptor by 3 to 6 orders of magnitude.

An N-alkylamine radiolabel photoprobe, N-(3-(3-Iodo,4-azidophenyl)propyl)octadecan-1-amine, was also prepared to identify the binding region(s) of these compounds on the sigma-1 receptor. Upon UV irradiation of the pure sigma-1 receptor in the presence of excess substituted phenylpropyl-N-alkylamine photoprobes, two populations were generated as evidenced by the appearance of 26 and 23 kDa bands on a polyacrylamide gel at a ratio of 1:1. Generation of these two sigma-1 receptor populations was dependent on photolysis of N-alkylamine derivatives of 12 carbons or longer having either N-(3-(4-nitrophenyl)propyl)- or N-(3-(4-azidophenyl)propyl)-moieties, and was protectable by haloperidol.

The 23 kDa population was not formed as a result of photo-chemical cleavage of the sigma-1 receptor because both of the N- and C-terminals are present as confirmed by N-terminal sequencing and Western analysis using an anti-C-term hexahistidine antibody. Using anti-sigma-1 receptor antibody, this property was detected in both guinea pig liver membranes and COS-7 cells overexpressing the sigma-1 receptor upon UV irradiation with N-(3-(4-Nitrophenyl)propyl)dodecan-1-amine. Together, these data reveal unique features of the sigma-1 receptor binding region(s).

Example 5

The Hallucinogen N,N-Dimethyltryptamine (DMT) is an Endogenous Sigma-1 Receptor Regulator The sigma-1 receptor is widely distributed in the central nervous system and periphery. Originally mischaracterized as an opioid receptor, the sigma-1 receptor binds to numerous synthetic compounds but does not bind opioid peptides; it is currently considered an orphan receptor. The sigma-1 receptor pharmacophore includes an alkylamine core, also found in the endogenous compound N,N-dimethyltryptamine (DMT). DMT acts as a hallucinogen, but its receptor target has remained unclear. DMT bound to sigma-1 receptors and inhibited voltage-gated Na$^+$ channels in both native cardiac myocytes and heterologous cells that express sigma-1 receptors. DMT also induced hypermobility in wild type mice but not in sigma-1 receptor knockout mice. These biochemical, physiological, and behavioral experiments indicate DMT as an endogenous agonist for the sigma-1 receptor.

The sigma-1 receptor binds a broad range of synthetic compounds (1). It has long been suspected that the sigma-1 receptor is targeted by endogenous ligands, and several candidates have been previously proposed (2, 3). Although progesterone and other neuroactive steroids are known to bind sigma-1 receptors and regulate some of their functions (1, 4), they do not exhibit agonist properties on ion channels in electrophysiological experiments (5).

Figure 5:
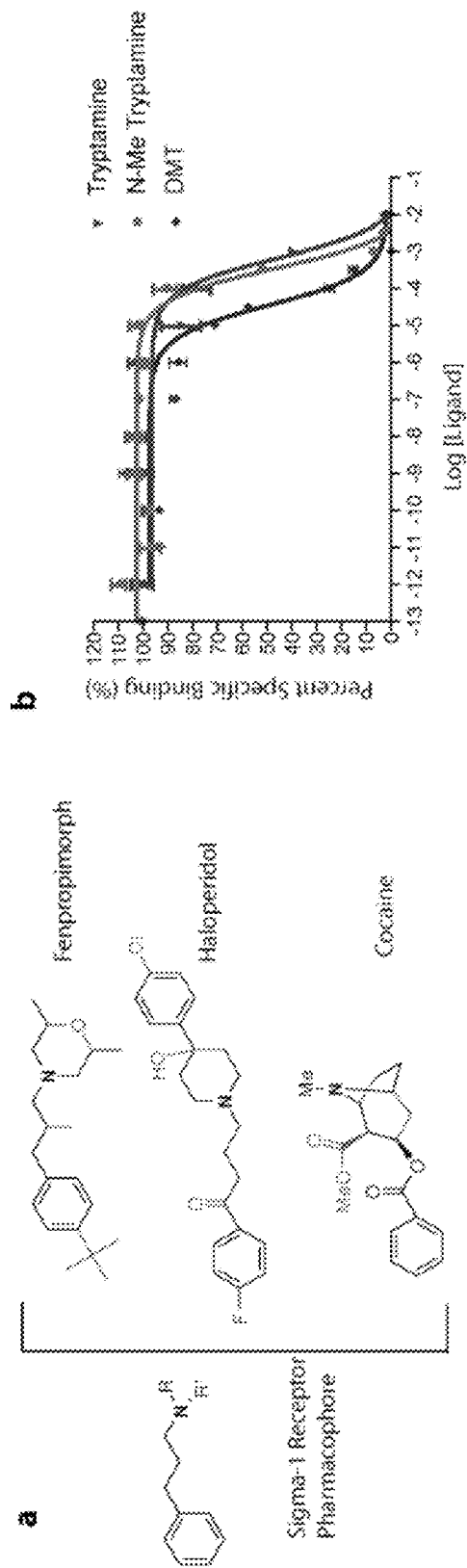
FIG. 5. Sigma-1 Receptor Ligand Pharmacophore and Binding Affinities. (a) A basic sigma-1 receptor ligand pharmacophore variant of Glennon et al. (6) was derived by removal of the red bonds from the sigma-1 receptor ligands, fenpropimorph, haloperidol, and cocaine. (b) Competitive binding curves of tryptamine, N-methyltryptamine, and DMT, against the radioactive sigma-1 receptor ligand [$^3$H]-(+)-pentazocine. Curves are shown as percent specific binding (5 µM haloperidol).

The analysis described herein for sigma receptor endogenous ligand(s) was based on a variant of the canonical sigma-1 receptor ligand pharmacophore (6), but is more basic in structure (FIG. 5a). Otherwise dissimilar sigma-1 receptor ligands possess a common N-substituted pharmacophore: an N,N-dialkyl or N-alkyl-N-aralkyl product, found in the high affinity sigma-1 receptor ligand, fenpropimorph (7), as well as in a general sense, haloperidol and cocaine. N-substituted trace amines harbor this sigma-1 receptor ligand pharmacophore, but their interactions with sigma receptors have not been determined.

The only known endogenous mammalian N,N-dimethylated trace amine is N,N-dimethyltryptamine (DMT) (8-10). DMT is one of the active compounds in psychoactive snuffs (yopo, epena) and sacramental teas (ayahuasca, yagé), and is used in native shamanic rituals in South America. DMT can also be produced by enzymes in mammalian lung (11) and in rodent brain (12). DMT has been found in human urine, blood, and cerebrospinal fluid (9, 13). While there are no conclusive quantitative studies measuring the abundance of endogenous DMT due to its rapid metabolism (14), DMT concentrations can be localized and elevated in certain instances. Evidence indicates that DMT can be locally sequestered into brain neurotransmitter storage vesicles and that DMT production increases in rodent brain under environmental stress(8).

Although a family of G-protein coupled receptors (GPCRs) known as the trace amine receptors (TAR) has been discovered in 2001 (15), only two members of this family respond to trace amines and have been renamed to trace amine-associated receptors (TAARs) (16). Because other binding targets for trace amines and DMT are likely(8), the sigma-1 receptor binding affinities of the trace amines and their N-methylated and N,N-dimethylated counterparts was first examined.

TABLE 4

Sigma-1 and sigma-2 receptor $K_d$ values of trace amines and their N-methylated and N,N-dimethylated derivatives (Scheme 5-1). Included are ±SEM values (n = 3) and $R^2$ values for a non-linear regression curve fit. Solid arrows denote the direction of increasing affinity.

| C | $R_1$ | $R_2$ | Ligand | Sigma-1R $K_D$ (µM) (±SEM, n = 3), $R^2$ | Sigma-2R $K_D$ (µM) (±SEM, n = 3), $R^2$ | Ratio Sigma2/Signal |
|---|---|---|---|---|---|---|
| | H— | H— | Tryptamine | 431.55 (±342.5, 0.87) | 4.91 (±5.2, 0.92) | 0.011 |
| | H— | H$_3$C— | N-methyltryptamine | 150 (±61.6, 0.97) | 12.82 (±7.0, 0.94) | 0.085 |
| | H$_3$C— | H$_3$C— | N,N'-dimethyl-tryptamine | 14.75 (±7.0, 0.96) | 21.71 (±10.8, 0.94) | 1.472 |

TABLE 4-continued

Sigma-1 and sigma-2 receptor $K_d$ values of trace amines and their N-methylated and N,N-dimethylated derivatives (Scheme 5-1). Included are ±SEM values (n = 3) and $R^2$ values for a non-linear regression curve fit. Solid arrows denote the direction of increasing affinity.

| C | $R_1$ | $R_2$ | Ligand | Sigma-1R $K_D$ (µM) (±SEM, n = 3), $R^2$ | Sigma-2R $K_D$ (µM) (±SEM, n = 3), $R^2$ | Ratio Sigma2/Signal |
|---|---|---|---|---|---|---|
| Phenethylamine structure | H—<br>H—<br>$H_3C$— | H—<br>$H_3C$—<br>$H_3C$— | Phenethylamine (PEA)<br>N-methylPEA<br>N,N'-dimethylPEA | 97.4 (±23.3, 0.99)<br>59.85 (±22.3, 0.96)<br>12.89 (±6.9, 0.92) | 7.31 (±5.2, 0.97)<br>21.93 (±12.5, 0.94)<br>21.16 (±11.8, 0.93) | 0.075<br>0.366<br>1.642 |
| Tyramine structure | H—<br>H—<br>$H_3C$—<br>H— | H—<br>$H_3C$—<br>$H_3C$—<br>ethyl | Tyramine<br>N-methyltyramine<br>N,N'-dimethyltyramine<br>N-ethyltyramine | >30000<br>12.43 (±2.7, 0.98)<br>38.27 (±10.3, 0.98)<br>1.62 (±0.5 0.97) | 607 (±422, 0.89)<br>6.61 (±10.6, 0.91)<br>64.29 (±43.0, 0.94)<br>N/A | >0.020<br>0.532<br>1.680<br>N/A |

Competition assays against the sigma-1 receptor specific ligand, (+)-[$^3$H]-pentazocine (10 nM) determined that the non-methylated trace amines tryptamine, phenethylamine, and tyramine bound the sigma-1 receptor poorly (Table 4), with $K_d$ values of 431.55 µM, 97.4 µM, and >30000 µM, respectively. By contrast, the N-methylated and N,N-dimethylated derivatives of these compounds bound sigma-1 receptors more tightly, with a clear increase in affinity as the ligands approached the sigma-1 receptor ligand pharmacophore (FIGS. 5a and 5b). With the exception of the N-methylated tyramines, this trend did not apply to the sigma-2 receptor, which differs pharmacologically and functionally from the sigma-1 receptor (Table 4).

Tryptamine, phenethylamine, and N-methyltyramine, had the highest sigma-2 receptor affinities with $K_d$ values of 4.91 µM, 7.31 µM, and 6.61 µM, respectively. In contrast to sigma-1 receptors, N-methylation and N,N-dimethylation of tryptamine and phenethylamine decreased sigma-2 receptor affinity (Table 4).

Figure 6:
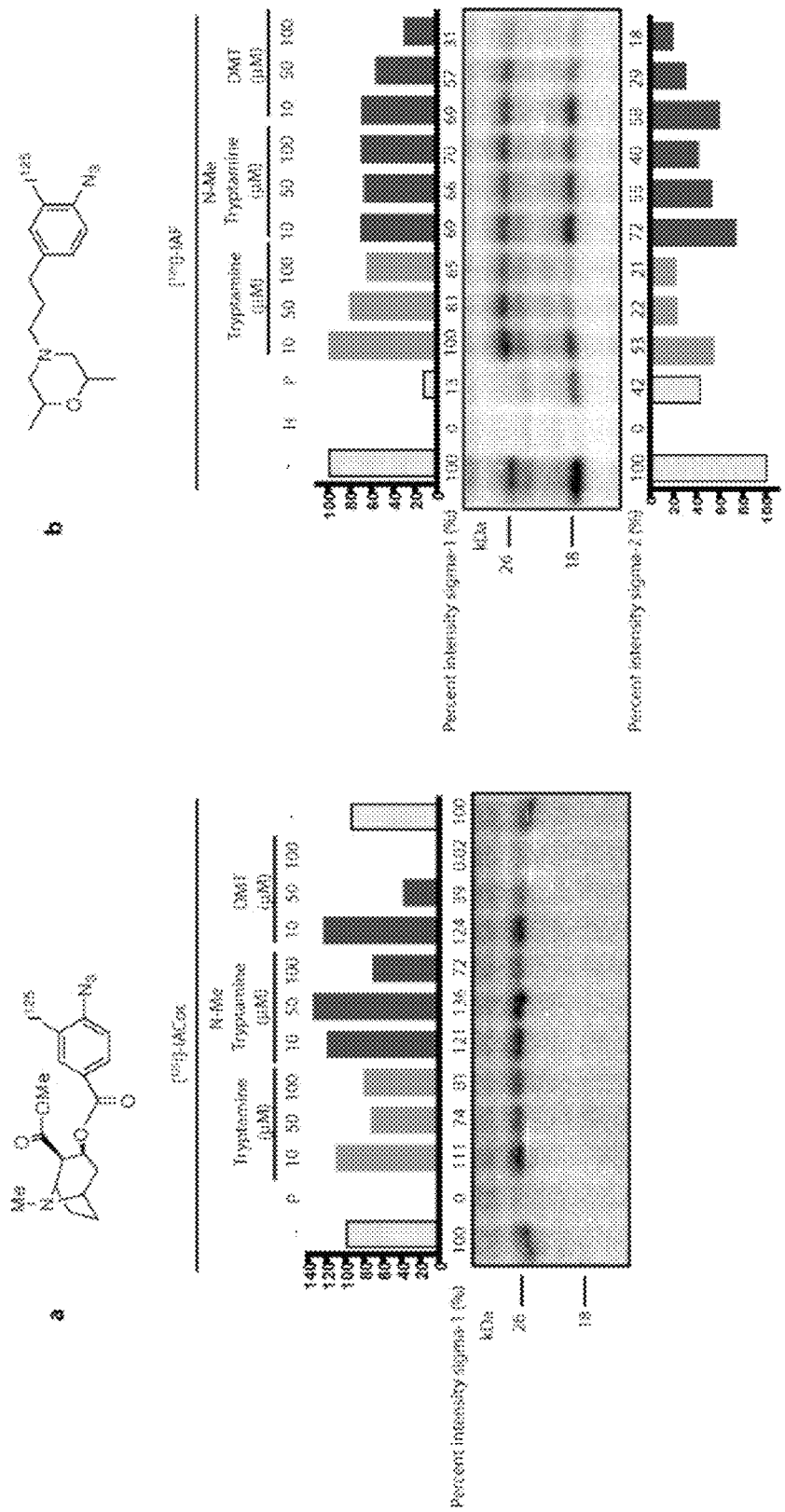
FIG. 6. Tryptamine, N-methyltryptamine, and DMT inhibition of photolabeling. Rat liver membranes (100 µg/lane) were suspended in the presence or absence of the protecting drugs. Samples were photolyzed with (a) 1 nM carrier-free [$^{125}$I]-IACoc or (b) 1 nM carrier-free [$^{125}$I]IAF. Ten µM (+)-pentazocine (P) protected sigma-1 receptor photolabeling while 10 µM haloperidol (H) protected both sigma-1 and sigma-2 receptors. Percent band intensities are shown compared to controls performed in the absence of protecting ligand (−).

The ability of tryptamine, N-methyltryptamine, and DMT to block sigma receptor photolabeling in rat liver homogenates were tested by two radioactive photoaffinity labels, the sigma-1 receptor specific cocaine derivative 3-[$^{125}$I]iodo-4-azidococaine ([$^{125}$I]-IACoc) (17) (FIG. 6a), and the sigma-1 and sigma-2 receptor fenpropimorph derivative 1-N-(2',6'-dimethyl-morpholino)-3-(4-azido-3-[$^{125}$I]iodo-phenyl)propane ([$^{125}$I]IAF) (18) (FIG. 6b). Both of these compounds have been used to identify the drug binding region of the sigma-1 receptor (18, 19).

[$^{125}$I]-IACoc (sigma-1 $K_d$=0.126 nM(17)) photolabeling of the 26 kDa sigma-1 receptor (FIG. 6a) was protected best by DMT, with 61% protection by 50 µM DMT and almost 100% protection by 100 µM DMT. On the other hand, tryptamine and N-methyltryptamine protected minimally against sigma-1 receptor [$^{125}$I]-IACoc photolabeling, even at these high concentrations (FIG. 6a). Similarly, [$^{125}$I]IAF photolabeling of the sigma-1 ($K_d$=194 nM (18)) receptor showed that DMT was the most potent protector. Ten µM DMT protected 31%, while 50 µM and 100 µM DMT protected 43% and 69%, respectively (FIG. 6b). With the exception of N-methyltryptamine, protection of [$^{125}$I]IAF sigma-2 ($K_d$=2780 nM(18)) receptor photolabeling paralleled the sigma-2 binding data. Tryptamine afforded the greatest protection of sigma-2 receptor photolabeling, with values of 47%, 78%, and 79% for 10, 50, and 100 µM, respectively (FIG. 6b).

An important biological activity of sigma receptor activation is the inhibition of ion channels, which operates through protein-protein interactions without mediation by G-proteins and protein kinases (20-22). In addition to modulating various types of voltage-activated $K^+$ channels (21, 23, 24), the sigma-1 receptor associates with the Kv 1.4 $K^+$ channel in posterior pituitary nerve terminals as well as in *Xenopus* oocytes (22). Sigma receptor ligands also modulate N-, L-, P/Q-, and R-type $Ca^{2+}$ channels in rat sympathetic and parasympathetic neurons (25). Sigma receptor ligands modulate cardiac voltage-gated $Na^+$ channels (hNav1.5) in HEK293 cells, COS-7 cells, and neonatal mouse cardiac myocytes (26).

Figure 7:
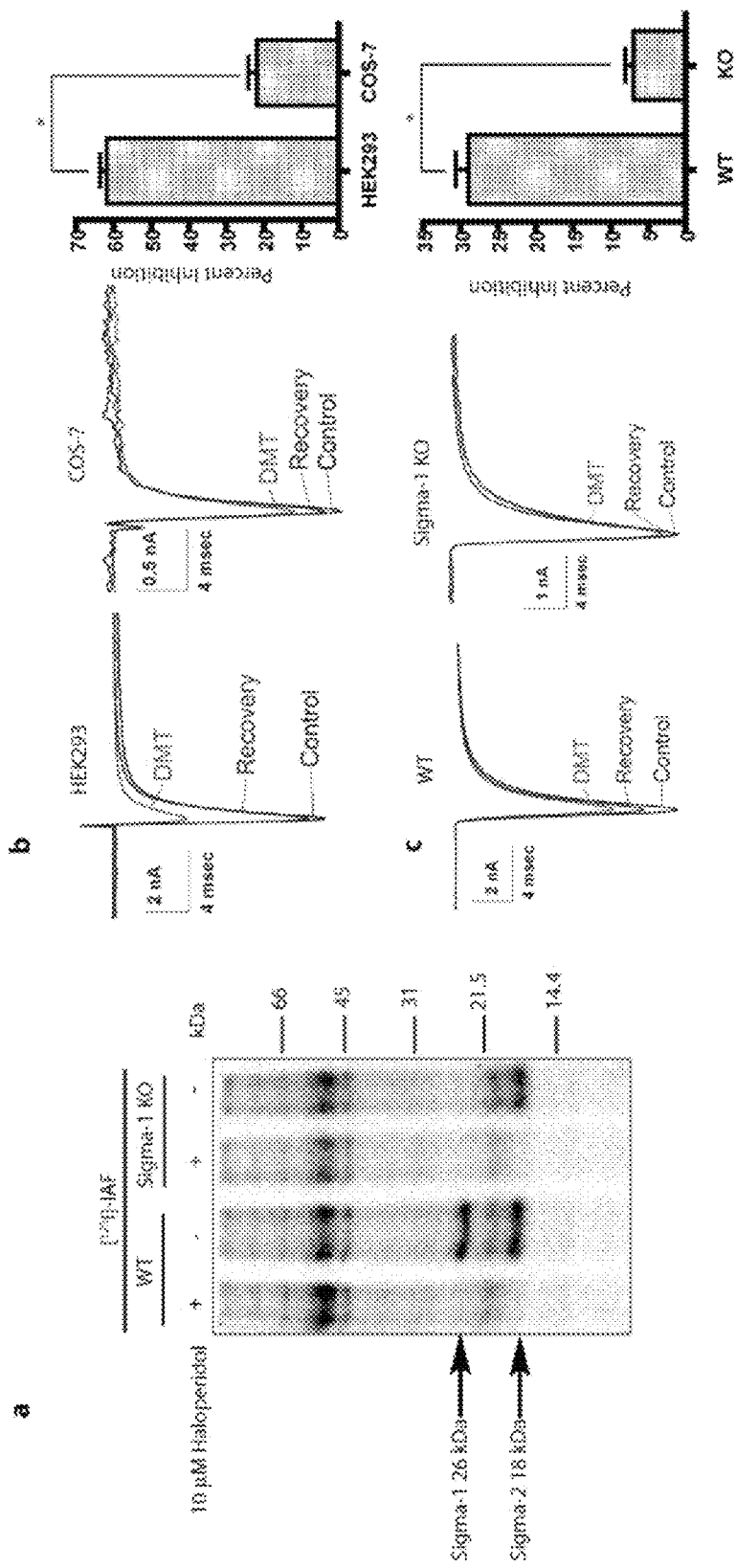
FIG. 7. Sodium channel inhibition by DMT. (a) In the presence or absence of 10 µM haloperidol, wild type (WT) or sigma-1 receptor knockout (KO) mouse liver homogenates (200 µg/lane) were photolabeled with [$^{125}$I]IAF. (b) Examples of $I_{Na}$ evoked by steps from −80 mV to −10 mV in HEK293 or COS-7 cells expressing hNav1.5 channel in the absence (control, black), presence (drug, red), and after wash out (recovery, blue) of 100 µM DMT. Average inhibition by DMT was determined by measuring peak $I_{Na}$. Bars represent mean±SEM (n=3). $I_{Na}$ inhibition in HEK293 cells differed significantly from that in COS-7 cells (*p<0.03). (c) Examples of $I_{Na}$ evoked as described in (b) in neonatal cardiac myocytes from WT and KO mice in the absence (control, black), presence (drug, red), and after wash out (recovery, blue) of 100 µM DMT. Current inhibition in WT was significantly different from that in KO (*p<0.002, n=7).

To evaluate the capacity of DMT to induce physiological responses by binding to sigma receptors, the action of DMT on voltage-activated $Na^+$ current was examined. Patch clamp recordings from HEK293 cells stably expressing the human cardiac $Na^+$ channel hNav1.5 revealed voltage activated $Na^+$ currents ($I_{Na}$) in response to voltage steps from −80 mV to −10 mV (FIG. 7b). Application of 100 µM DMT inhibited $I_{Na}$ by 62±3% (n=3), which reversed upon DMT removal. With hNav1.5 transiently transfected into COS-7 cells, 100 µM DMT inhibited $I_{Na}$ by only 22±4% (n=3), but photolabeling has shown that these cells have much lower levels of endogenous sigma-1 receptor compared to HEK293 cells (26) (FIG. 7b).

The difference between DMT inhibition of $I_{Na}$ in HEK293 and COS-7 cells (FIG. 7b, p<0.03) thus demonstrates the dependence of $I_{Na}$ inhibition on sigma-1 receptors. Experiments in cardiac myocytes demonstrated the same DMT action in a native preparation (FIG. 7c), and enabled further demonstration of sigma-1 receptor dependence by using a sigma-1 receptor knockout mouse (27). [$^{125}$I]IAF photolabeling of liver homogenates from wildtype (WT) and sigma-1 receptor knockout (KO) mice indeed showed the absence of sigma-1 receptor (26 kDa) in the KO samples (FIG. 7a). In WT neonatal cardiac myocytes, 100 µM DMT reversibly inhibited $I_{Na}$ by 29±3% (n=7), while $I_{Na}$ was reduced by only 7±2% (n=7) in KO myocytes (FIG. 7c, p<0.002).

Both DMT and sigma receptor ligands influence animal behavior. DMT injection induces hypermobility in rodents concurrently treated with the monoamine oxidase inhibitor (MAOI), pargyline (28), and this action is not antagonized by blockers of dopamine or 5-HT receptors, but is potently inhibited by haloperidol (28). Although haloperidol is thought to act in part through the dopamine $D_2$ receptor system, it is also a potent sigma-1 receptor agonist (sigma-1 $K_i=3$ nM(29); sigma-2 $K_i=54$ nM (29)) when inhibiting voltage-gated ion channels (5, 25). Haloperidol reduces brain levels of DMT (8) and DMT inhibits haloperidol binding in brain tissue more robustly than the dopamine agonist, apomorphine (8). Based on these findings, which were discovered before sigma receptor identification, DMT has been hypothesized to act through an unknown "hallucinogen" receptor (8). Results (28) that intraperitoneal administration of DMT (2 mg/kg) two hours after pargyline (75 mg/kg, i.p.) injection induced hypermobility in WT mice (7025±524.1 cm, n=12) in an open-field assay were confirmed.

Figure 8:
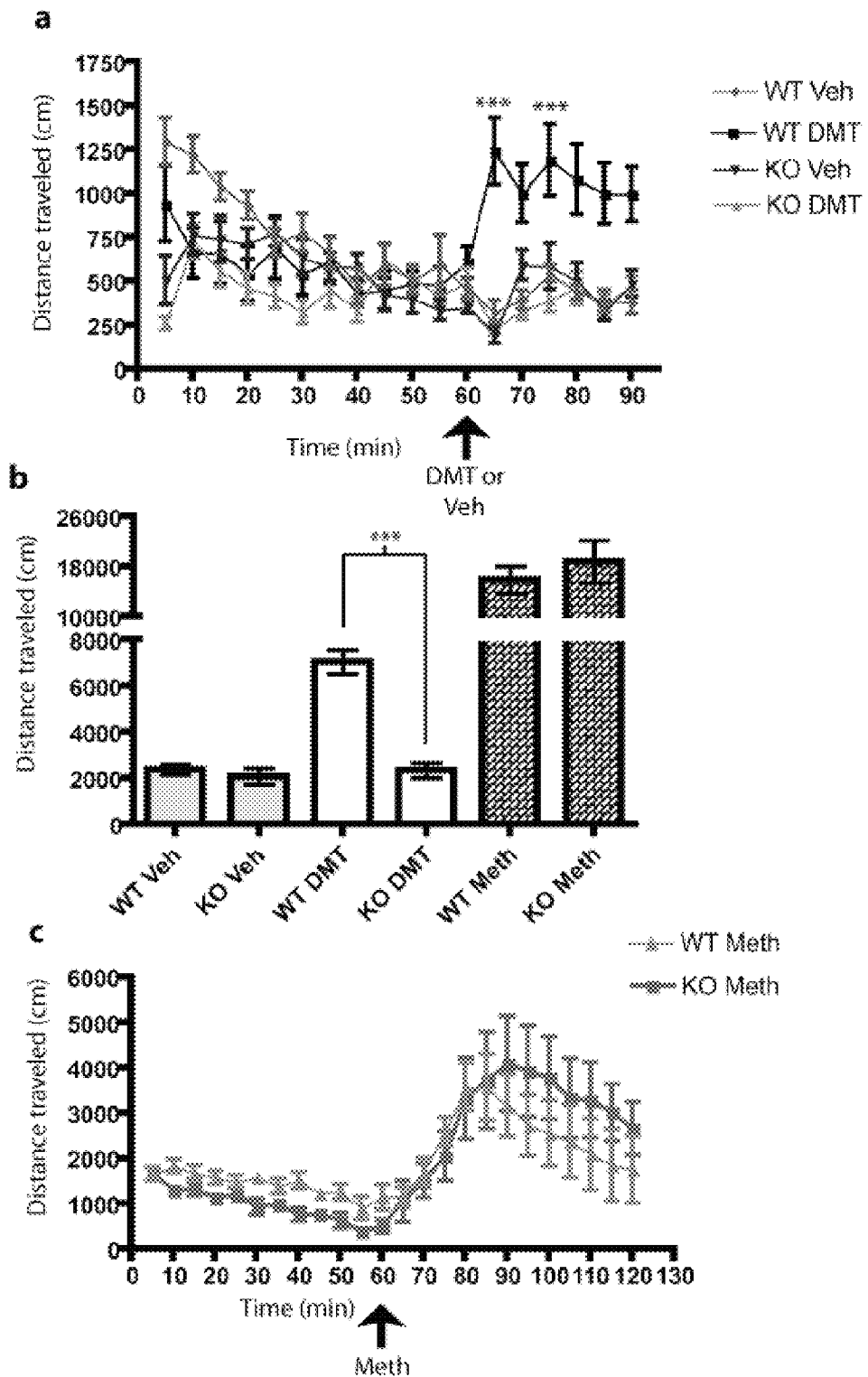
FIG. 8. DMT induced hypermobility abrogated in the sigma-1 KO mouse. (a) Distances traveled by WT and KO mice were measured in an open-field assay in 5 min increments. Pargyline was injected two hours prior to DMT or vehicle (Veh) i.p. injection. Bars represent mean±SEM (n=8-14). WT mice showed a significant (***p<0.0001) increase in mobility in response to DMT compared to KO mice. (b) Total distance traveled over 30 minutes following DMT, vehicle (Veh), or methamphetamine (Meth, n=6) injection in WT and KO mice. (c) Methamphetamine serves as a positive control for hypermobility in KO mice.

Identical drug treatments in sigma-1 receptor KO mice had no hypermobility action (2328±322.9 cm, n=12, p<0.0001, FIGS. 8a and 8b). This result is important to the understanding of sigma-1 receptor biological function because the KO mice are viable and fertile (27). The sigma-1 receptor dependence of DMT-induced hypermobility parallels that induced by the sigma-1 receptor ligand (+)-SKF10047 in WT but not in KO mice (27). As a positive control, methamphetamine, which is thought to act through dopamine systems, induced hypermobility in both WT and KO mice (3 mg/kg, i.p., n=6, FIGS. 8b and 8c) with a reduced onset rate than that seen for DMT (FIGS. 8a and 8c). This indicates that behavioral actions of DMT depend on the sigma-1 receptor, which may provide an alternative research area for psychiatric disorders that have not been linked to dopamine or NMDA systems.

The binding, biochemical, physiological, and behavioral studies reported here all indicate that DMT acts as a ligand for the sigma-1 receptor. Based on binding results and the sigma-1 receptor pharmacophore, endogenous trace amines and their N-methyl and N,N-dimethyl derivatives can to serve as endogenous sigma receptor regulators. Moreover, DMT, the only known mammalian N,N-dimethylated trace amine, can activate the sigma-1 receptor to modulate $Na^+$ channels.

The recent discovery that the sigma-1 receptor functions as a molecular chaperone (30) may be relevant, because sigma-1 receptors, which are observed in the endoplasmic reticulum, associate with plasma membrane Kv 1.4 channels (22) and may serve as a molecular chaperone for ion channels. Furthermore, the behavioral effect of DMT may be due to activation or inhibition of sigma-1 receptor chaperone activity instead of, or in addition to, DMT/sigma-1 modulation of ion channels. These studies thus indicate that this natural hallucinogen could exert its action by binding to sigma-1 receptors, which are abundant in the brain (1, 27). This discovery may also extend to N,N-dimethylated neurotransmitters such as the psychoactive serotonin derivative, N,N-dimethylserotonin (bufotenine), which has been found at elevated levels in the urine of schizophrenic patients (10). DMT and sigma-1 receptors therefore act as a ligand-receptor pair.

The invention therefore provides a method of administering a compounds as described herein to a mammal to modulate sigma-1 receptor activity. The modulation can promote cell growth, for example when the compound is DMT, or a derivative thereof. In various embodiments, the compounds described herein act by selective binding to the sigma-1 receptor over the sigma-2 receptor. In other embodiments, the compounds described herein act as ion channel modulators and can activate the sigma-1 receptor.

Chemistry.

Yields refer to isolated pure products after column chromatography. The products were characterized by comparison of their spectral (IR, $^1$H and $^{13}$C NMR, elemental and mass spectroscopy analyses) and physical data with those of authentic samples. $^1$H NMR spectra were recorded at 300 MHz in $CDCl_3$ relative to TMS (0.00 ppm). Melting points were determined with a Thomas-Hoover capillary melting point apparatus and are reported uncorrected. The synthesis of compounds 1-5 is outlined in Scheme 5-1.

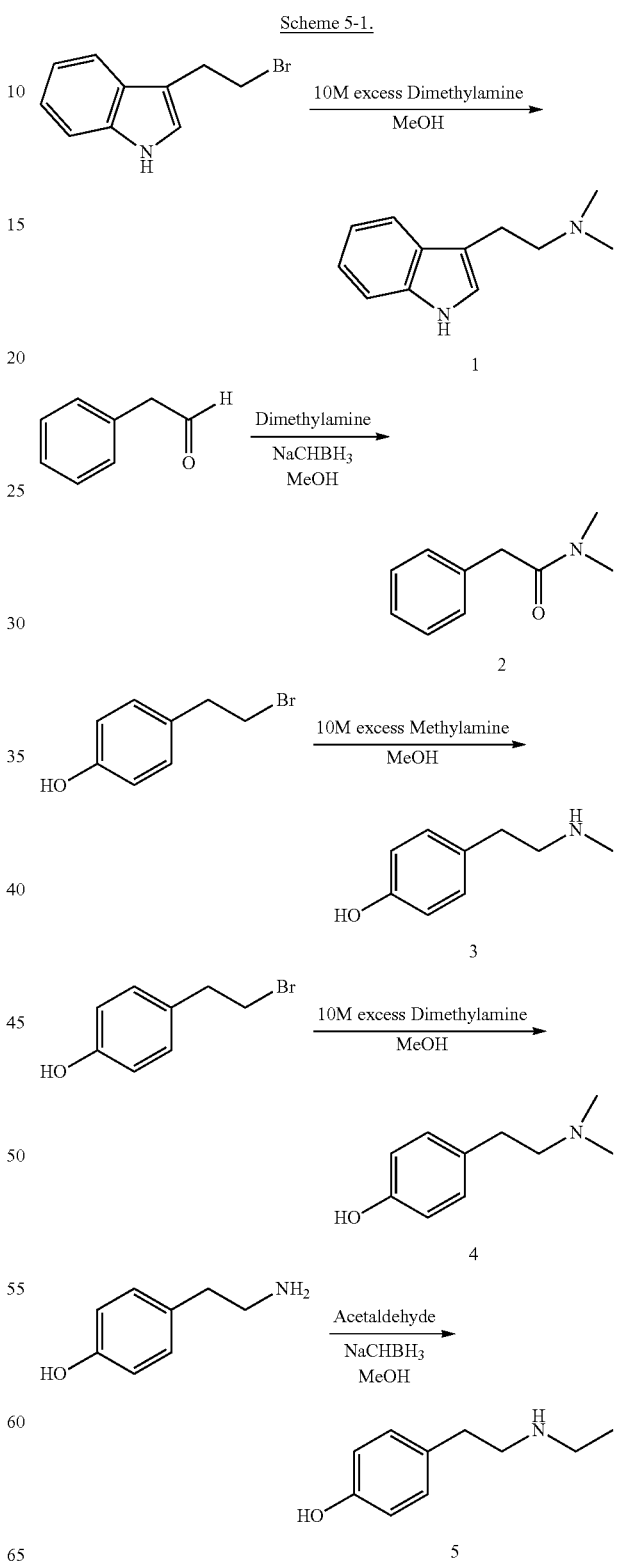

Scheme 5-1.

Preparation of 2-(1H-indol-3-yl)-N,N-dimethylethylamine (1)

To 250 mg of 3-(2-bromoethyl)indole in a round-bottomed flask, a 10 M excess of dimethylamine (6 mL of 2M in MeOH) was added and the solution was stirred at r.t. overnight. After adding 5 mL sodium bicarbonate (2%), the reaction mixture was extracted with chloroform (3×5 ml) and back extracted with $H_2O$ (1×5 mL). The combined extracts were dried over $MgSO_4$ and evaporation of the solvent gave the product in crystalline form. Yield: 0.21 g, 84%, yellowish crystals. m.p.: 45-47° C.; TLC (EtAc:MeOH:acetic acid, 8:2:0.5 v/v/v): RF=0.33. $^1H$ NMR, δ: 10.43 (s, 1H), 7.42-7.06 (m, 5H), 2.68 (m, 4H), 2.26 (S, 6H). $^{13}C$ NMR ($CDCl_3$): δ 136.5, 124.3, 123.2, 121.2, 119.7, 117.6, 113.4, 111.1, 61.7, 41.2, 22.4. Anal. calcd for $C_{12}H_{16}N_2$: C, 76.55; H, 8.57; N, 14.88%. Found; C, 76.60; H, 8.70; N, 14.70%.

Preparation of N,N-dimethyl-2-phenylethylamine (2)

To a stirring solution of phenylacetaldehyde (5 mM, 0.6 mL) and dimethylamine (5 mM, 3 mL of 2M in MeOH) in MeOH (1 mL), was added $NaCNBH_3$ (5 mM, 360 mg) in a round-bottomed flask. The reaction mixture was stirred at room temperature overnight. The solvent was evaporated and $H_2O$ was added to the residue before extraction with $CH_2Cl_2$. The combined extracts were dried over $MgSO_4$, the solid was filtered off, and the solvent was evaporated under reduced pressure to give a yellow oil. The crude products were purified by column chromatography (silica gel, EtAc:n-hexane, 4:6) to afford pure product in quantitative yield, 0.52 g, 87%, yellow oil. TLC (EtAc:n-hex, 4:6 v/v): RF=0.2. $^1H$ NMR, δ: 7.40-7.20 (m, 5H), 3.20 (m, 4H), 2.20 (S, 6H). $^{13}C$ NMR, δ: 141.5, 129.1, 128.6, 125.8, 60.9, 45.6, 32.2. Anal. calcd for $C_{10}H_{13}N$: C, 80.48; H, 10.13; N, 9.39%. Found; C, 90.60; H, 10.20; N, 9.40%.

Preparation of 4-(2-(methylamino)ethyl)phenol (3)

To 250 mg of 4-hydroxyphenethyl bromide in a round-bottomed flask, a 10 M excess of $MeNH_2$ (6.2 mL of 2M in MeOH) was added and the solution was stirred at r.t. overnight. After filtration, the solvent was removed to give a brown oil in 80% yield. TLC (EtAc:MeOH, 9:1 v/v): RF=0.33. $^1H$ NMR, δ: 9.42 (s, 1H), 7.10 (d, 2H), 6.75 (d, 2H), 3.60 (s, 3H), 2.84 (t, 2H), 2.60 (t, 2H), 1.90 (s, 1H). $^{13}C$ NMR, δ: 167.5, 131.2, 128.3, 112.4, 41.5, 36.4, 35.0. Anal. calcd for $C_9H_{13}NO$: C, 71.49; H, 8.67; N, 9.26%. Found; C, 71.50; H, 8.80; N, 9.20%.

Preparation of 4-(2-(dimethylamino)ethyl)phenol (4)

To 250 mg of 4-hydroxyphenethyl bromide in a round-bottomed flask, a 10 M excess of methylamine (6.22 mL of 2M in MeOH) was added and the solution was stirred at r.t. overnight. After filtration, the solvent was evaporated and gave the product in crystalline form in 92% yield, 0.23 g, light yellow. m.p.: 73-76° C. TLC (EtAc:MeOH, 9:1 v/v): RF=0.1. $^1H$ NMR, δ: 9.43 (s, 1H), 7.12 (d, 2H), 6.70 (d, 2H), 2.74 (m, 4H), 2.30 (s, 6H). $^{13}C$ NMR, δ: 167.5, 134.3, 130.2, 115.6, 60.6, 45.9, 32.4. Anal. calcd for $C_{10}H_{15}NO$: C, 72.69; H, 9.15; N, 8.48%. Found; C, 72.60; H, 9.30; N, 8.40%.

Preparation of 4-(2-(ethylamino)ethyl)phenol (5)

To a stifling solution of tyramine (1 mM, 137 mg) and MeOH (5 mL) was added acetaldehyde in excess. Then excess $NaBH_3CN$ (1 mM, 62.8 mg) was added and the mixture stirred for 2 hours at r.t. After evaporating the solvent, methylene chloride (5 mL) was added and mixture was washed with $H_2O$ (3×5 mL). The mixture was dried over $MgSO_4$, filtered, and evaporated to give the product in 72% yield as an orange oil. TLC (toluene:diethylamine, 4:1 v/v): RF=0.5. $^1H$ NMR, δ: 9.48 (s, 1H), 7.14 (d, 2H), 6.70 (d, 2H), 2.85 (m, 2H), 2.60 (t, 2H), 250 (q, 2H), 2.1 (s, 1H), 1.1 (t, 3H). $^{13}C$ NMR, δ: 167.5, 134.3, 130.2, 115.6, 48.2, 44.4, 35.6, 15.6. Anal. calcd for $C_{10}H_{15}NO$: C, 72.69; H, 9.15; N, 8.48%. Found; C, 72.50; H, 9.20; N, 8.50%.

Radiochemistry.

Radiosynthesis of 3-[$^{125}$I]iodo-4-azidococaine ([$^{125}$I]-IACoc) (17) and 1-N-(2',6' dimethyl-morpholino)-3-(4-azido-3-[$^{125}$I]iodo-phenyl)propane ([$^{125}$I]IAF) (18) was performed as described.

Preparation of Rat/Guinea Pig/Mouse Liver Membranes.

Preparation of rat, guinea pig, and mouse liver membrane homogenates was performed as previously described (18, 31) with the exception that mouse livers were obtained from age-matched adult 129/SvEvBrd x C57BL6/J sigma-1 receptor knock out (27) and wild-type mice.

Cell Culture and Transfection.

HEK293 cells stably expressing hNav1.5 were provided by Dr. J. C. Makielski at the University of Wisconsin-Madison (32). COS-7 cells were transiently transfected with recombinant cDNA encoding hNav1.5 using Lipofectamine. Both cell types were cultured on glass coverslips at 37° C. in 5% $CO_2$/air atmosphere, and used for electrophysiological recordings within 3-5 days.

Neonatal Myocyte Isolation and Culture.

Neonatal mouse cardiac myocytes were enzymatically isolated and cultured on laminin-coated glass coverslips as previously described (33, 34) with minor changes (26).

Sigma Receptor Binding Assays.

Competitive binding assays were performed as previously described (18) with the exception of testing new ligands shown in Table 4.

Photoaffinity Labeling.

Sigma-1 and sigma-2 receptors were photolabeled with 3-[$^{125}$I]iodo-4-azidococaine ([$^{125}$I]-IACoc) and 1-N-(2',6'-dimethyl-morpholino)-3-(4-azido-3-[$^{125}$I]iodo-phenyl) propane ([$^{125}$I]IAF) as described (18) with the exception of the protecting ligands, tryptamine, N-methyltryptamine, and N,N-dimethyltryptamine (DMT).

Electrophysiology.

$I_{Na}$ was recorded using whole-cell patch clamp at room temperature. All patch clamp solutions used as well as patch clamp methodology and instrumentation details are previously described (26) with the exception of testing $I_{Na}$ inhibition with 100 μM DMT.

Mouse Behavior.

All mice were maintained on a normal light/dark cycle and handled in accordance with Animal Care and Use Guidelines of the University of Wisconsin, Madison. Hypermobility effects induced by DMT in age-matched adult 129/SvEvBrd xC57BL6/J wild type (WT) and sigma-1 receptor knockout (KO) mice were measured in an open-field assay. Mice were first acclimatized to the experimental room for one hour. WT and KO mice were injected with the monoamine oxidase inhibitor, pargyline (75 mg/kg, i.p.) two hours prior to DMT or vehicle injection(28). The mice were observed in the open-field box for an hour and then injected with DMT (2 mg/kg, i.p.) (28) or vehicle, and observed for 30 minutes. Each condition represents 8 to 14 mice (n=8-14). For methamphetamine studies, WT and KO mice (n=6) were placed in the open-field and observed for one hour prior to methamphetamine (3 mg/kg, i.p.) injection (35) and observation (1 hour). A computer program was used to quantitate movement and after each experiment, 70% ethanol was used to remove odors from the open-field.

Cited Documents

1. T. Hayashi, T. P. Su, *CNS Drugs* 18, 269 (2004).
2. P. Bouchard et al., *Eur J Neurosci* 7, 1952 (Sep. 1, 1995).
3. T. P. Su, A. D. Weissman, S. Y. Yeh, *Life Sci* 38, 2199 (Jun. 16, 1986).
4. T. P. Su, E. D. London, J. H. Jaffe, *Science* 240, 219 (Apr. 8, 1988).
5. R. A. Wilke et al., *J Physiol* 517 (Pt 2), 391 (Jun. 1, 1999).
6. R. A. Glennon et al., *J Med Chem* 37, 1214 (Apr. 15, 1994).
7. F. F. Moebius, R. J. Reiter, M. Hanner, H. Glossmann, *Br J Pharmacol* 121, 1 (May, 1997).
8. S. A. Barker, J. A. Monti, S. T. Christian, *Int Rev Neurobiol* 22, 83 (1981).
9. F. Franzen, H. Gross, *Nature* 206, 1052 (Jun. 5, 1965).
10. M. S. Jacob, D. E. Presti, *Med Hypotheses* 64, 930 (2005).
11. J. Axelrod, *Science* 134, 343 (Aug. 4, 1961).
12. J. M. Saavedra, J. Axelrod, *Science* 175, 1365 (Mar. 24, 1972).
13. J. M. Beaton, P. E. Morris, *Mech Ageing Dev* 25, 343 (June, 1984).
14. S. A. Burchett, T. P. Hicks, *Prog Neurobiol* 79, 223 (August, 2006).
15. B. Borowsky et al., *Proc Natl Acad Sci USA* 98, 8966 (Jul. 31, 2001).
16. L. Lindemann et al., *Genomics* 85, 372 (March, 2005).
17. J. R. Kahoun, A. E. Ruoho, *Proc Natl Acad Sci USA* 89, 1393 (Feb. 15, 1992).
18. A. Pal et al., *Mol Pharmacol* 72, 921 (October, 2007).
19. Y. Chen, A. Hajipour, M. Sievert, M. Arbabian, A. Ruoho, *Biochem.* 46, 3532 (Mar. 20, 2007).
20. P. J. Lupardus et al., *J Physiol* 526 Pt 3, 527 (Aug. 1, 2000).
21. H. Zhang, J. Cuevas, *J Pharmacol Exp Ther* 313, 1387 (June, 2005).
22. E. Aydar, C. P. Palmer, V. A. Klyachko, M. B. Jackson, *Neuron* 34, 399 (Apr. 25, 2002).
23. R. A. Wilke et al., *J Biol Chem* 274, 18387 (Jun. 25, 1999).
24. C. Kennedy, G. Henderson, *Neuroscience* 35, 725 (1990).
25. H. Zhang, J. Cuevas, *J Neurophysiol* 87, 2867 (June, 2002).
26. M. Johannessen, Ramachandran S., Ramos-Serrano, A., Ruoho, A. E., and Jackson, M. B., *Am J Physiol Cell Physiol* Submitted, (2008).
27. F. Langa et al., *Eur J Neurosci* 18, 2188 (October, 2003).
28. P. Jenner, C. D. Marsden, C. M. Thanki, *Br J Pharmacol* 69, 69 (May, 1980).
29. R. R. Matsumoto, B. Pouw, *Eur J Pharmacol* 401, 155 (Aug. 4, 2000).
30. T. Hayashi, T. P. Su, *Cell* 131, 596 (Nov. 2, 2007).
31. D. Fontanilla et al., *Biochemistry* 47, 7205 (Jul. 8, 2008).
32. C. R. Valdivia, T. Nagatomo, J. C. Makielski, *J Mol Cell Cardiol* 34, 1029 (August, 2002).
33. R. C. Balijepalli et al., *Proc Natl Acad Sci USA* 103, 7500 (May 9, 2006).
34. H. B. Nuss, E. Marban, *J Physiol* 479 (Pt 2), 265 (Sep. 1, 1994).
35. E. C. Nguyen et al., *Neuropharmacology* 49, 638 (October, 2005).

Accordingly, the invention provides compounds, compositions, and methods for administering an agonist of the sigma-1 receptor to a mammal to provide an agonistic effect, such as hypermobility. Administration of a compound described herein can also treat an addition, such as an opioid addiction or a cocaine addiction. Additionally, $F^{18}$-labeled compounds described herein can be used for imaging sigma-1 receptors and various tumors.

Example 6

N,N'-Alkylamines and N-Alkyl-N'-Arylalkylamines Bind to the Sigma-1-Receptor

The design, synthesis, and evaluation of the relative affinities of several N,N'-dialkyl or N-alkyl-N'-arylalkyl compounds to the sigma-1 receptor are reported in this Example by competition assays against (+)-[$^3$H]-pentazocine and to the sigma-2 receptor using [$^3$H]-ditolyl guanidine ([$^3$H]-DTG) (Pal; Hajipour; Fontanilla; Ramachandran; Chu; Mavlyutov; Ruoho. *Mol Pharmacol* 2007). The high affinity N,N'-dialkyl or N-alkyl-N'-arylalkyl compounds were evaluated in cytotoxicity assays for their ability to inhibit the growth of various tumor cell lines.

The synthesized N,N'-dialkyl (compounds 1-11, Scheme 6-1) or N-alkyl-N'-aralkyl compounds (compounds 13-18, Scheme 6-2) were tested for their binding affinities to sigma-1 receptors in guinea pig liver membranes, and to sigma-2 receptors in rat liver membranes, as summarized in Tables 6-1 and 6-2.

Scheme 6-1. N,N'-Dialkyl Compounds.

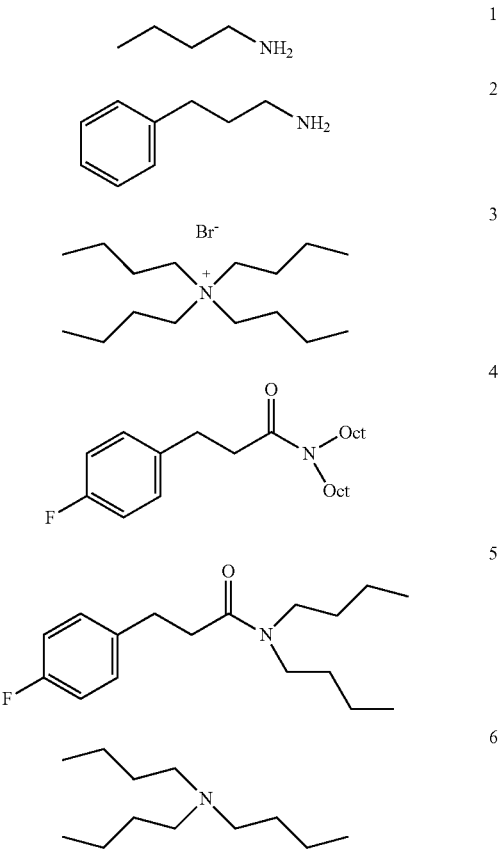

-continued
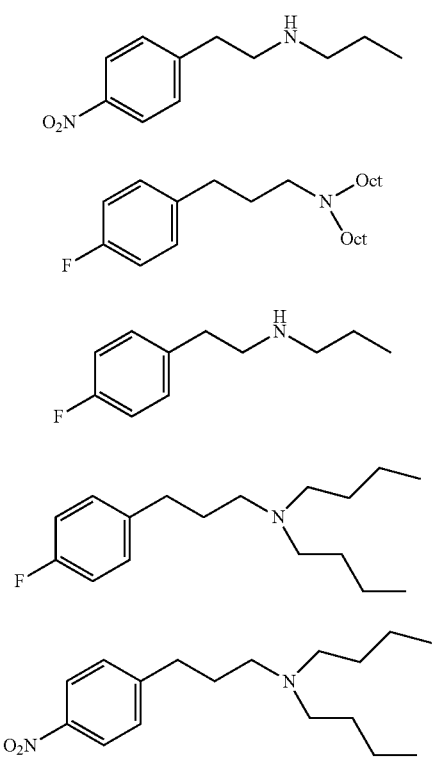
Scheme 6-1. N-Alkyl-N'-Arylalkyl Compounds.
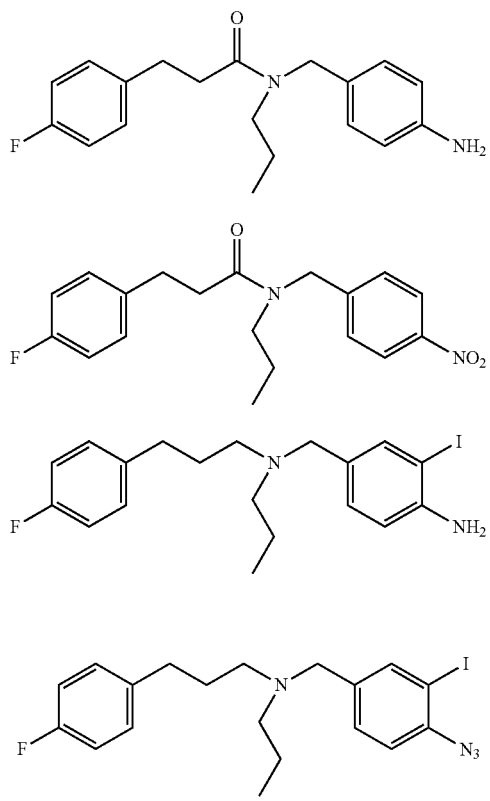
-continued
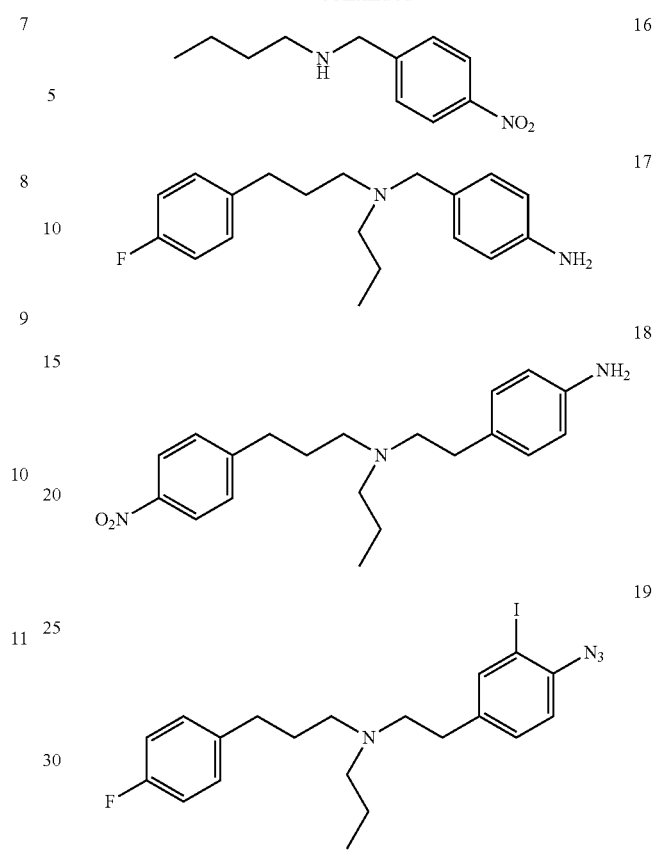
TABLE 1
Binding affinities of N,N'-dialkyl derivatives
| Ligand | Sigma 1 $K_D$ values (nM) (±SEM, n = 3), $R^2$ value | Sigma2 $K_D$ values (nM) (±SEM, n = 3), $R^3$ value | Ratio (σ2/σ1) |
|---|---|---|---|
| 1 | >50000000 | [a] | nd[b] |
| 2 | 68865 (±1.12, 0.98) | 269666 | 3.92 |
| 3 | 54702 (±1.15, 0.97) | 268000 | 4.90 |
| 4 | 53579 (±1.12, 0.98) | [a] | nd[b] |
| 5 | 32063 (±1.24, 0.94) | 126333 | 3.94 |
| 6 | 6998 (±1.11, 0.99) | 44842 | 6.41 |
| 7 | 2254 (±1.2, 0.95) | 53617 | 23.8 |
| 8 | 665.3 (±1.13, 0.98) | 1653 (±1.69, 0.96) | 2.49 |
| 9 | 91 (±1.16, 0.97) | 230 (±1.75, 0.90) | 2.53 |
| 10 | 17.7 (±1.07, 0.99) | 685 (±1.17, 0.98) | 38.7 |
| 11 | 0.3 (±1.29, 0.96) | 404 (±1.21, 0.97) | 1347 |
[a]Does not compete with [$^3$H]-Pentazocine or [$^3$H]-DTG
[b]nd—not determined

TABLE 2

Binding affinities of N-alkyl-N'-aralkyl derivatives

| Ligand | Sigma 1 $K_D$ values (nM) (±SEM, n = 3), $R^2$ value | Sigma 2 $K_D$ values (nM) (±SEM, n = 3) $R^3$ value | Ratio (σ2/σ1) |
|---|---|---|---|
| 13 | a | 236000 | nd[b] |
| 14 | 393000 | 133200 (±1.59, 0.87) | 0.3389 |
| 15 | 89000 (±1.21, 0.96) | >50000000 | 570.8 |
| 16 | 1151 (±1.14, 0.98) | 1683 (±1.93, 0.94) | 1.4622 |
| 17 | 164 (±1.16, 0.97) | 2150 (±1.79, 0.93) | 13.11 |
| 18 | 6 (±1.21, 0.96) | 83.6 (±1.68, 0.85) | 13.93 |
| 19[c] | 7240 (±2.03, 0.98)[c] | 1290 (±3.4, 0.96)[c] | 0.178[c] |
| 20[c] | 2590 (±0.63, 0.96)[c] | 120 (±0.045, 0.91)[c] | 0.046[c] |

[a]Does not compete with [$^3$H]-Pentazocine or [$^3$H]-DTG
[b]nd—not determined
[c]Fontanilla, D. et al. Biochemistry 2008, 47, 7205-7217.

The binding affinities of these compounds were determined by competitive displacement of [$^3$H]-(+)-pentazocine (10 nM) and showed high affinity and selectivity to the sigma-1 receptor. For determination of binding to the sigma-2 receptor, 3 nM [$^3$H]-ditolyl guanidine (DTG) was utilized in the presence of non-radioactive (+)-pentazocine (100 nM), which masked the sigma-1 receptor population from binding to [$^3$H]-DTG. Non-specific binding was determined by adding 5 mM Haloperidol as a control condition. Curve fitting using "GraphPad Prism version 4.0C" indicated that all the compounds fit to a single binding site for the sigma-1 receptor with regression values ($R^2$) between 0.94 and 0.99 (Tables 6-1 and 6-2). Selectivity ratios between the sigma-1 receptor and the sigma-2 receptor were also calculated to determine relative specificity and are summarized in Tables 6-1 and 6-2.

With the exception of compound 14, the compounds which were synthesized based on a proposed sigma-1 receptor ligand pharmacophore (Fontanilla; Johannessen; Hajipour; Cozzi; Jackson; Ruoho. Science 2009, 323, 934) generally had a higher affinity and specificity for the sigma-1 receptor than for the sigma-2 receptor. Specific binding of compounds 4, 5, and 13, either could not be detected to bind to the sigma-1 receptor ($K_D$>100000 nM) or possessed very low affinity, presumably because the amide group present in these compounds traps the nitrogen's lone pair, which is needed for optimal sigma receptor binding as previously reported by the Glennon group (Bioorg. Med. Chem. 2000, 8, 2105). The importance of the nitrogen's lone pair is further illustrated by comparing the $K_D$ values of compounds 5(32063 nM) with 10(17.7 nM) and 4(53579 nM) with 8 (665.3 nM), showing a 2000-fold and 100-fold affinity difference, respectively. In contrast, compounds 10, 11, and 18 were found to be exceptionally high affinity compounds for the sigma-1 receptor with $K_D$ values of 17.7 nM, 0.3 nM, and 6 nM, respectively.

The nitro substituent on the phenyl ring of compound 18 likely enhances binding to the sigma-1 receptor due to its greater electron withdrawing character as demonstrated by the 400-fold difference in affinity between compound 18 (6 nM) and N-propyl-N-(4-aminophenyl-ethyl)-3-(4-fluorophenyl)propylamine (sigma-1 $K_D$=2590 nM), which contains a fluorine atom replacing the nitro group. In a similar manner, addition of a nitro group on the phenyl ring of the high affinity compound 10 (sigma-1 $K_D$=17.7 nM), further improves binding to the sigma-1 receptor as demonstrated by compound II (sigma-1 $K_D$=0.3 nM). Compound 13 clearly demonstrates that compounds with amide groups, even in the presence of a nitro-substituent on the phenyl ring, effectively prevented sigma-1 receptor binding, providing further evidence that the nitrogen's lone pair is vital for optimal sigma-1 receptor binding.

Because sigma-1 receptors are overexpressed in numerous tumor cell lines, which include breast cancer, lung carcinoma, renal carcinoma, colon carcinoma, sarcoma, brain tumors, melanoma, glioblastoma, neuroblastoma, and prostate cancer, the ability of the compounds to inhibit the growth of various tumor cell lines were tested. Cytotoxicity assays revealed that the N,N'-dialkyl or N-alkyl-N'-arylalkyl compounds are cytotoxic against a number of cancer cells lines (Table 6-3) including breast, lung, prostate, ovarian, colorectal, and CNS, indicating their utility as potential anti-cancer or diagnostic agents.

Figure 9:
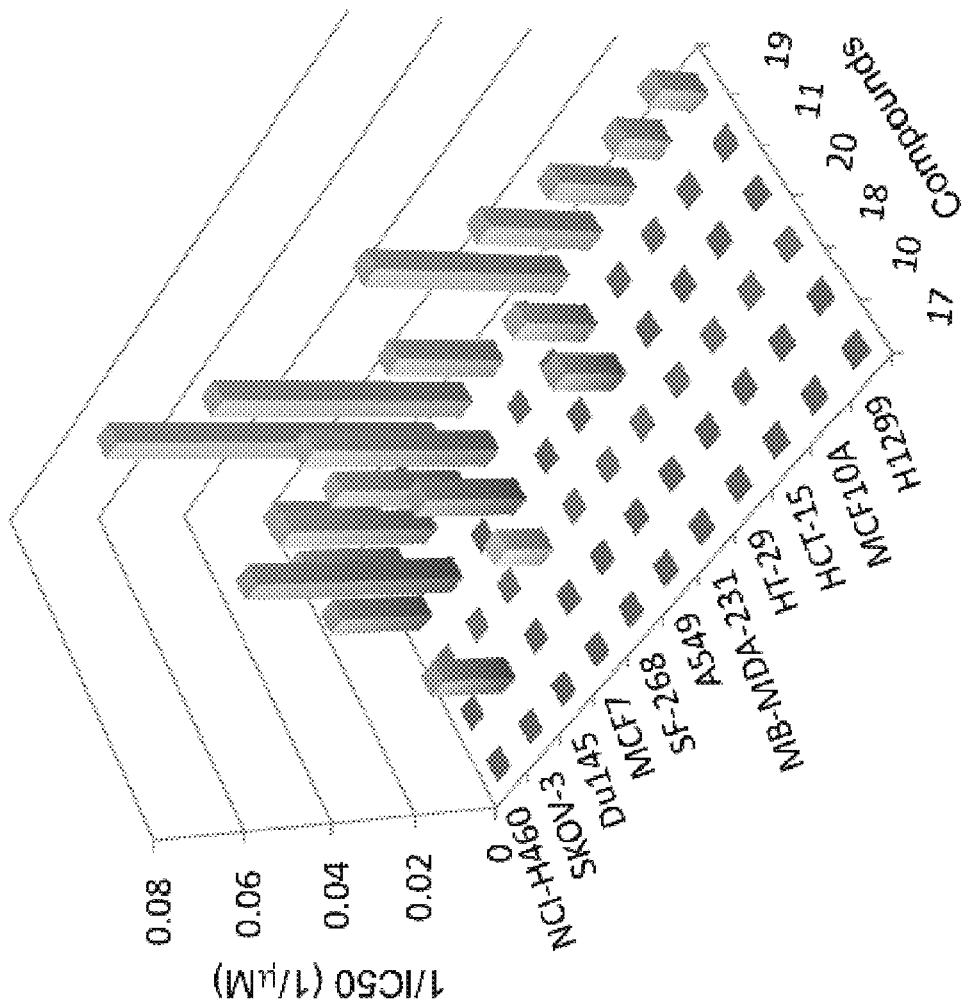
FIG. 9. Compounds 10, 11, 17, 18, 19, and 20 were used in cytotoxicity assays to measure their ability to inhibit growth of various tumor cells. The graphical representation of $1/IC_{50}$ of the compounds plotted against the various tumor cell lines is illustrated. $IC_{50}$ values of the compounds are reported in tabular form in Table 6-3.

Compounds 10, 11, 17, 18, 19, and 20 (Schemes 6-1 and 6-2) were tested based on their high affinities and specificities for the sigma-1 receptor. Except for compound 17, the chosen N,N'-dialkyl or N-alkyl-N'-aralkyl derivatives inhibited cell growth in vitro (Table 6-3). As illustrated in FIG. 9, compound 19 was non-specifically cytotoxic in almost all the cell lines tested, whereas compound 17 lacked any cytotoxic properties. Furthermore, only specific cell lines were susceptible to compounds 10, 11, 18, and 20. Cell lines that seemed to have the greatest susceptibility to the N,N'-dialkyl or N-alkyl-N'-aralkyl compounds were NCI-H460 (human lung adenocarcinoma), SKOV-3 (human ovarian adenocarcinoma), MCF7 (human breast adenocarcinoma), and MB-MDA-231 (human breast adenocarcinoma).

Correlation between the cytotoxicity growth inhibition levels and the sigma receptor binding affinities is less clear due to unknown involvement of the sigma-1 versus sigma-2 receptor with regard to these novel compounds. Though structurally similar except for a nitro substituent (Scheme 2), compound II has a higher affinity and higher selectively for the sigma-1 receptor than compound 10 (Table 6-1), and robustly inhibits growth in MB-MDA231, MCF7, Du145, and NCI-H460 cell lines in addition to SKOV-3 cells, the only cell line whose growth is inhibited by compound 10. Compounds 20 and 18 do not follow the same trend as compounds 10 and 11. While compound 20 has a higher binding affinity for the sigma-2 receptor than the sigma-1 receptor (Table 6-2), it is cytotoxic to more tumor cell lines than the structurally similar compound 18, which has high affinity for sigma-1 (Table 6-3). FIG. 9 illustrates graphical representation of 1/IC$_{50}$ of the compounds plotted against the various tumor cell lines

TABLE 6-3

Growth Inhibition of Tumor Cell Lines. Compounds 10, 11, 17, 18, 19, and 20 were used in cytotoxicity assays to measure their ability to inhibit growth of various tumor cells. $IC_{50}$ values of the compounds are reported in tabular form.

| Carcinoma type | Cell Line | Compound 17 IC50 (um) (SE) | Compound 10 IC50 (uM) (SE) | Compound 18 IC50 (uM) (SE) | Compound 20 IC50 (uM) (SE) | Compound 11 IC50 (uM) (SE) | Compound 19 IC50 (uM) (SE) |
|---|---|---|---|---|---|---|---|
| HU lung | NCI-H460 | >100 | >100 | >100 | 44.77 (7.81) | 40.52 (4.86) | 40.32 (5.61) |
| HU Ovarian | SKOV-3 | >100 | 56.18 (6.74) | >100 | 20.15 (5.34) | 27.85 (5.13) | >100 |
| HU Prostate | Du145 | >100 | >100 | >100 | >100 | 32.67 (1.62) | 13.06 (0.58) |
| HU Breast | MCF7 | >100 | >100 | 86.1 (6.41) | 41.34 (1.75) | 22.38 (1.86) | 16.75 (1.46) |
| HU CNS | SF268 | >100 | >100 | >100 | >100 | >100 | 38.8 (1.62) |
| HU lung | A549 | >100 | >100 | >100 | >100 | >100 | >100 |
| HU Breast | MB-MDA-231 | >100 | >100 | >100 | 86.12 (3.03) | 57.12 (4.72) | 21.6 (0.96) |
| HU Colorectal | HT-29 | >100 | >100 | >100 | >100 | >100 | 36.42 (1.16) |
| HU Colorectal | HCT-45 | >100 | >100 | >100 | >100 | >100 | 54.12 (7.84) |
| HU Breast | MCP10A | >100 | >100 | >100 | >100 | >100 | 86.63 (7.38) |
| HU Lung | HI299 | >100 | >100 | >100 | >100 | >100 | 90.81 (4.44) |

The findings from this study show that N,N'-dialkyl and N-alkyl-N'-arylalkyl fenpropimorph-like compounds are sigma ligands that exhibit increased sigma-1 receptor affinity with the addition of electron withdrawing nitro substituents. Alternatively, sigma-1 receptor affinity is abolished when an amide group is introduced into the compound structure. Furthermore, these fenpropimorph-like compounds exhibit specific cytotoxic activity against numerous tumor cell lines, demonstrating their ability to be used as clinical anti-cancer, imaging, and/or diagnostic agents.

Chemistry.

Yields refer to isolated pure products after column chromatography. The products were characterized by comparison of their spectral (IR, $^1$H and $^{13}$C NMR, CHN and Mass spectroscopy Analysis) and physical data with those of authentic samples. $^1$H NMR spectra were recorded at 300 MHz in $CDCl_3$ relative to TMS (0.00 ppm) and IR spectra were recorded on a Shimadzu 435 IR spectrometer. Melting points were determined with a Thomas-Hoover capillary melting point apparatus and are reported uncorrected. Chemicals were obtained from Aldrich Chemical Co. and utilized without further purification. Elemental analysis was performed at the Research Institute of Petroleum Industry, Tehran, IR, Iran.

Preparation of 3-(4-nitrophenyl)-propylbromide 2 g of $P_2O_5$/silica gel (65% w/w) (10 mmol) (Hajipour; Kooshki; Ruoho. Tetrahedron Letters 2005, 46, 5503) and 3-phenylpropylbromine (10 mmol, 1.98 g) was ground for 30 seconds, and then 5 mL of $HNO_3$ 65% was added. The mixture was ground with a pestle at r.t. until a deep-yellow color appeared (2 minutes). When TLC analysis (n-hexane:EtOAc 90:10) showed complete disappearance of 3-phenylpropylbromide (10 min), ether (100 ml) was added to the reaction mixture and the solid was separated through a short pad of silica gel and washed with ether (3×20 mL). The filtrate was washed with 10% $NaHCO_3$ (3×20 mL) and dried ($MgSO_4$). The solvent was evaporated under reduced pressure and the residue was purified by short column chromatography (n-Hexane:EtOAc, 90:10). 3-(4-nitrophenyl)-propylbromide was obtained (8.3 mmol, 2.02 g 83%) as a yellow oil. $^1$H NMR ($CDCl_3$): δ 8.2 (d, J=6.3), 7.38 (d, 2H, 6.3), 3.3 (t, 2H, J=7.8), 2.55 (t, 2H, J=7.8), 2.12 (m, 2H). $^{13}$C NMR ($CDCl_3$): δ 145.7, 144.9, 129.7, 123.5, 36.7, 34.7, 32.4. Anal. Calculated for $C_9H_{10}BrNO_2$: C, 44.29H, 4.13; N, 5.74%. Actual: C, 44.50; H, 48.30; N, 5.80%.

General Procedure for Preparation of Amides 5, 4, and 13.

A mixture of DCC (1 mmol, 2.1 g) and 4-fluorophenylpropionic acid (0.17 g, 1 mmol) was ground with a pestle in a mortar for 30 seconds and then the amine (1 mmol) was added to the reaction mixture. The reaction was ground with a pestle until TLC showed no remaining acid (n-hexane:EtOAc, 75:25) (20 min). Then to the reaction mixture was added a mixture of ether (20 mL) and $H_2O$ (5 mL). The ether layer was washed with saturated $NaHCO_3$, dried ($MgSO_4$), and evaporated by a rotary evaporator to give a residue. The residue was purified by column chromatography (silica gel, n-hexane: EtOAc, 75:25).

N,N-Dibutyl-3-(4-fluorophenyl)propionamide (5)

Yield: (0.26 g, 93%), mp. 162-164° C. IR (KBr): 1658 $cm^{-1}$. $^1$H NMR ($CDCl_3$): δ 7.2-6.7 (m, 4H), 3.13 (t, 2H), 2.95 (t, 2H), 2.4 (t, 4H), 1.45 (m, 8H), 0.90 (t, 6H). MS (CI) m/z 279 (100, M$^+$). Anal. Calculated for $C_{17}H_{26}FNO$: C, 73.08; H, 9.38; N, 5.01%. Actual: C, 72.90; H, 9.40; N, 5.20%.

N,N-Dioctyl-3-(4-fluorophenyl)propionamide (4)

Yield: (0.37 g, 95%), mp. 190-193° C. IR (KBr): 1663 $cm^{-1}$. $^1$H NMR ($CDCl_3$): δ 7.2 (m, 2H), 6.7 (m, 2H), 3.20 (t, 4H, J=7.8), 2.95 (t, 2H, J=7.8), 2.51 (t, 2H, J=7.8), 1.50 (m, 4H), 1.29 (m, 20H), 0.90 (t, 6H, J=7.8). $^{13}$C NMR ($CDCl_3$): δ 173.1, 159.16, 133.80, 129.80, 115.40, 47.90, 47.70, 34.23, 32.85, 31.64, 30.03, 29.50, 27.75, 23.10, 14.04. MS (CI) m/z 391.6 (100, M$^+$). Anal. Calculated for $C_{25}H_{42}FNO$: C, 76.68; H, 10.81; N, 3.58%. Actual: C, 76.40; H, 10.90; N, 3.40%.

N-Propyl-N-(4-nitro-benzyl)-3-(4-fluorophenyl)propionamide (13)

Yield: (0.30 g, 86%), Yellow oil. IR (KBr): 1661 $cm^{-1}$. $^1$H NMR ($CDCl_3$): δ 8.07 (d, 2H, J=6.8), 7.32 (d, 2H, J=6.8), 7.10 (m, 2H), 6.92 (m, 2H), 4.42 (s, 2H), 3.20 (t, 2H, J=7.8), 2.83 (t, 2H, J=7.8), 2.61 (t, 2H, J=7.8), 1.69 (m, 2H), 0.96 (t, 3H, J=7.8). $^{13}$C NMR ($CDCl_3$): δ 173.90, 159.31, 146.71, 135.81, 129.04, 123.44, 115.41, 53.33, 49.61, 34.21, 31.83, 22.36, 11.41. MS (CI) m/z 344 (100, M$^+$). Anal. Calculated for $C_{19}H_{21}FN_2O_3$: C, 66.27; H, 6.15; N, 8.13%. Actual: C, 66.10; H, 6.30; N, 8.10%.

General Procedure for Preparation of Amines 7 and 16:

To a stifling mixture of 3-(4-nitophenyl)ethylbromide or 4-nitrobenzyl bromide (1 mmol), $Et_3N$ (1.1 mmol, 0.11 g) in $Et_2O$ (10 ml) was added N-propyl or N-butyl amine (3 mmol).

The reaction mixture was stirred at room temperature for 10 h. After filtration, the solvent was removed to give a yellow residue. The crude products were purified by column chromatography (silica gel, Toluene:Et$_2$NH, 20:1) to afford pure product.

N-propyl-N-3-(4-nitrophenyl)-ethylamine (7)

M.p. 142-144° C. Yield 86% (0.18 g, 0.86 mmol). IR (KBr): 3261 cm$^{-1}$. $^1$H NMR (CDCl$_3$): δ 8.14 (d, 2H, J=6.8), 7.38 (d, 2H, J=6.8), 2.89 (t, 2H, J=7.8), 2.67 (t, 2H, J=7.8), 2.56 (t, 2H, J=7.8), 2.02 (s, 1H, NH), 1.45 (m, 2H), 0.96 (t, 3H, J=7.8). $^{13}$C NMR (CDCl$_3$): δ 146.62, 146.31, 128.82, 123.50, 61.72, 61.45, 37.48, 26.51, 11.45. MS (CI) m/z 208 (100, M$^+$). Anal. Calculated for C$_{11}$H$_{16}$N$_2$O$_2$: C, 63.44; H, 7.74; N, 13.45%. Actual: C, 63.30; H, 7.90; N, 13.20%.

N-Butyl-N-4-nitrobenzylamine (16)

Pale yellow oil, b.p. 120-122° C. (15 mm Hg). Yield 80% (0.18 g, 0.80 mmol). IR (KBr): 3268 cm$^{-1}$. $^1$H NMR (CDCl$_3$): δ 8.14 (d, 2H, J=6.8), 7.38 (d, 2H, J=6.8), 3.81 (s, 2H), 2.67 (t, 2H, J=7.8), 2.02 (s, 1H, NH), 1.41-1.33 (m, 4H), 0.96 (t, 3H, J=7.8). $^{13}$C NMR (CDCl$_3$): δ 146.68, 146.30, 128.82, 123.50, 61.72, 49.25, 37.48, 44.42, 20.63, 13.72. MS (CI) m/z 208 (100, M$^+$). Anal. Calculated for C$_{11}$H$_{16}$N$_2$O$_2$: C, 63.44; H, 7.74; N, 13.45%. Actual: C, 63.40; H, 7.80; N, 13.20%.

General Procedure for Reduction of Nitro Groups of Compound 13 to the Corresponding Amino Group 12:

A mixture of nitro compounds (1 mmol) and 10 mg of Pd/C (10%) in methanol was reduced with H$_2$ at normal pressure. The mixture was stirred at room temperature over night. After filtration, solvent was removed to give a yellow residue. The crude products were purified by column chromatography (silica gel, Toluene:Et$_2$NH, 20:1) to afford pure amine.

N-Propyl-N-(4-amino-benzyl)-3-(4-fluorophenyl) propionamide (12)

Yield: (0.30 g, 94%), Semisolid. IR (KBr): 3258, 1661 cm$^{-1}$. $^1$H NMR (CDCl$_3$): 7.10 (m, 2H), 6.92 (m, 2H), δ 6.81 (d, 2H, J=6.8), 6.34 (d, 2H, J=6.8) 4.40 (s, 2H), 4.06 (s, 2H, NH$_2$), 2.83 (t, 2H, J=7.8), 2.51 (t, 2H, J=7.8), 1.59 (m, 2H), 0.96 (t, 3H, J=7.8). $^{13}$C NMR (CDCl$_3$): δ 173.90, 159.31, 146.71, 135.81, 129.04, 123.44, 115.41, 53.33, 49.61, 34.21, 31.83, 22.36, 11.41. MS (CI) m/z 314 (100, M$^+$). Anal. Calculated for C$_{19}$H$_{23}$FN$_2$O: C, 72.58; H, 7.37; N, 8.91%. Actual: C, 72.50; H, 7.50; N, 8.70%

General Procedure for Compound 18:

To a stirring mixture of 3-(4-nitophenyl)propylbromide (1 mmol), Et$_3$N (1.1 mmol, 0.11 g) in Et$_2$O (10 ml) was added N-propyl-N-4-aminobenzylamine or N-propyl-N-4-aminophenylethylmine (3 mmol). The reaction mixture was stirred at room temperature for 10 h. After filtration, solvent was removed to give a yellow residue. The crude products were purified by column chromatography (silica gel, Toluene:Et$_2$NH, 20:1) to afford pure product.

N-Propyl-N-4-aminophenylethyl-3-(4-nitrophenyl) propylamine (18); Semisolid

Yield 94% (0.32 g, 0.94 mmol). $^1$H NMR (CDCl$_3$): δ 8.14 (d, 2H, J=6.8), 7.38 (d, 2H, J=6.8), 6.81 (d, 2H, J=6.8), 6.35 (d, 2H, J=6.8), 4.02 (s, 2H, NH$_2$), 2.65-2.36 (m, 10H), 1.72 (m, 2H), 1.43 (m, 2H), 0.96 (t, 3H, J=7.8). $^{13}$C NMR (CDCl$_3$): δ 146.70, 144.93, 145.31, 129.92, 129.23, 123.70, 114.85, 59.70, 56.02, 55.21, 53.41, 33.58, 32.28, 22.78, 11.72. MS (CI) m/z 341 (100, M$^+$). Anal. Calculated for C$_{20}$H$_{22}$N$_3$O$_2$: C, 71.41; H, 6.59; N, 12.49%. Actual: C, 71.40; H, 6.60; N, 12.40%.

General Procedure for Reduction of Amides 5, 4, and 12 to the Corresponding Amines 10, 8, and 17:

In a double-necked round bottomed flask equipped with septum and condenser, a solution of amides (1 mmol) in anhydrous THF (5 ml) was added via a syringe dropwise to a stirred solution of LiAlH$_4$ (0.74 g, 2 mmol) in anhydrous THF (5 mL) under argon. TLC indicated the reaction to be almost completed after 15 min at room temperature. The reaction mixture was driven to completion by brief refluxing (15 min) and when it was cooled to r.t., it was diluted by adding 5 ml THF. The excess LiAlH$_4$ was destroyed by dropwise addition of water (1 mL), 15% aqueous NaOH (1 ml), and finally water (1 mL). The reaction mixture was stirred for 30 min at r.t. and then the solids were removed by filtration. The filtrate was dried (MgSO$_4$), and the solvent evaporated by a rotary evaporator to give pure products as yellow oils in quantitative yield.

N,N-Dibutyl-3-(4-fluorophenyl)propylamine (10)

$^1$H NMR (CDCl$_3$): δ 7.10 (m, 2H), 6.92 (m, 2H), 2.56 (t, 2H, J=7.8), 2.36 (m, 6H), 1.72 (m, 2H), 1.33 (m, 4H), 0.90 (t, 6H, J=7.8). MS (CI) m/z 265 (100, M$^+$). $^{13}$C NMR NMR (CDCl$_3$): δ 159.62, 134.39, 12993, 115.64, 63.88, 33.60, 32.27, 32.20, 20.81, 13.67. Anal. Calculated for C$_{17}$H$_{28}$FN: C, 76.93; H, 10.63; N, 5.28%. Actual: C, 77.90; H, 10.70; N, 5.20%.

N,N-Dioctyl-3-(4-fluorophenyl)propylamine (8)

$^1$H NMR (CDCl$_3$): δ 7.2 (m, 2H), 6.7 (m, 2H), 2.55 (t, 2H, J=7.8), 2.30 (m, 6H), 1.72 (m, 2H), 1.33-1.20 (m, 24H), 0.90 (t, 6H, J=7.8). $^{13}$C NMR (CDCl$_3$): δ 173.1, 159.16, 133.80, 129.80, 115.40, 47.90, 47.70, 34.23, 32.85, 31.64, 30.03, 29.50, 27.75, 23.10, 14.04. MS (CI) m/z 358.6 (100, M$^+$). Anal. Calculated for C$_{25}$H$_{44}$N: C, 83.73; H, 12.37; N, 3.91%. Actual: C, 83.60; H, 12.50; N, 3.80%.

N-Propyl-N-(4-amino-benzyl)-3-(4-fluorophenyl) propylamine (17)

3258 cm$^{-1}$. $^1$H NMR (CDCl$_3$): 7.10 (m, 2H), 6.92 (m, 2H), δ 6.81 (d, 2H, J=6.8), 6.34 (d, 2H, J=6.8), 4.06 (s, 2H, NH$_2$), 3.62 (s, 2H), 2.36 (m, 6H), 1.72 (m, 2H), 1.43 (m, 2H), 0.96 (t, 3H, J=7.8). $^{13}$C NMR (CDCl$_3$): δ 159.41, 145.23, 134.40, 129.39, 128.30, 115.57, 114.79, 59.73, 56.05, 34.51, 32.13, 22.76, 11.73. MS (CI) m/z 300 (100, M$^+$). Anal. Calculated for C$_{19}$H$_{25}$FN$_2$: C, 75.96; H, 8.39; N, 9.32%. Actual: C, 75.70; H, 8.40; N, 9.30%.

General Method for Iodination of Amine 17 to the Corresponding Amino Iodo Derivative 14:

A mixture of amines 21 or 19 (0.5 mmol) and tetramethylammonium dichloroiodate (0.5 mmol, 0.14 g) (Hajipour; Arbabian; Ruoho. *J. Org. Chem.* 2002, 67, 8622.) in a mortar was ground with a pestle to produce a homogenous powder and the mixture was left at room temperature until TLC (Toluene:Et$_2$NH, 20:1) showed complete disappearance of amines. To the brown solid was added 5 mL sodium bisulfate (5%) and the reaction mixture was extracted with dichloromethane (3×5 mL). The combined extracts were dried with MgSO$_4$. Evaporation of the solvent gave the corresponding iodo derivatives (15 or 17). The product was purified by column chromatography (silica gel, Toluene:Et$_2$NH, 20:1).

N-Propyl-N-(4-amino-3-iodo-benzyl)-3-(4-fluorophenyl)propylamine (14)

Oil, 84% yield. IR (KBr): 3245 cm$^{-1}$. $^1$H NMR (CDCl$_3$): 7.10-6.11 (m, 7H), 4.11 (s, 2H, NH$_2$), 3.62 (s, 2H), 2.65-236 (m, 6H), 1.72 (m, 2H), 1.43 (m, 2H), 0.96 (t, 2H, J=7.8). $^{13}$C NMR (CDCl$_3$): δ 159.41, 146.10, 138.70, 134.36, 129.89, 128.70, 127.93, 116.44, 115.04, 83.94, 59.40, 58.32, 43.47, 33.60, 32.13, 22.76, 11.73. MS (CI) m/z 426 (100, M$^+$). Anal. Calculated for C$_{19}$H$_{24}$IFN$_2$: C, 53.53; H, 5.67; N, 6.57%. Actual: C, 53.40; H, 6.70; N, 6.40%.

General Procedure for Conversion of Amino Iodo Derivative 14 to the Corresponding Azido Iodo Derivative 15:

To a cold mixture (0° C.) of 15 or 17 (0.1 mmol) in H$_2$O (2 mL), concentrated HCl (0.4 mL) was added with an aqueous solution of NaNO$_2$ (0.30 mmol, 21 mg, in 0.5 mL H$_2$O) in 5 min in a round bottomed flask. The reaction mixture stirred at room temperature for 30 min. Then to the reaction mixture at r.t. and darkness was added an aqueous solution of NaN$_3$ (0.36 mmol, 23 mg, in 0.5 mL H$_2$O) dropwise. The reaction mixture was stirred at r.t., and darkness for 30 min and then extracted with EtOAc (3×3 mL). The combined EtOAc solution was dried with MgSO$_4$ and the solvent was evaporated with rotary evaporator to afford an orange oil. The crude product was purified by column chromatography (silica gel, first toluene: Et$_2$NH, 20:1 and then toluene: Et$_2$NH, 4:1) to give the product as a yellow liquid.

N-Propyl-N-(4-azido-benzyl)-3-(4-fluorophenyl) propylamine (15)

Oil, 98% yield. $^1$H NMR (CDCl$_3$): 7.40-6.90 (m, 7H), 3.92 (s, 2H), 2.65-236 (m, 6H), 1.72 (m, 2H), 1.43 (m, 2H), 0.96 (t, 3H, J=7.8). $^{13}$C NMR (CDCl$_3$): δ 159.41, 138.14, 136.13, 134.42, 130.12, 129.90, 128.13, 115.57, 97.12, 59.30, 56.02, 53.40, 33.50, 32.13, 22.76, 11.73. MS (CI) m/z 452 (100, M$^+$). Anal. Calculated for C$_{19}$H$_{22}$IFN$_4$: C, 50.45; H, 4.90; N, 12.39%. Actual: C, 50.40; H, 5.00; N, 12.40%.

Preparation N,N-Dibutyl-3-(4-nitrohenyl)propylamine (11)

To a stirring mixture of 3-(4-nitophenyl)propylbromide (1 mmol), Et$_3$N (1.1 mmol, 0.11 g) in Et$_2$O (10 ml) was added N-dibutyl amine (3 mmol). The reaction mixture was stirred at room temperature for 10 hours. After filtration, the solvent was removed to give a yellow residue. The crude products were purified by column chromatography (silica gel, Toluene:Et$_2$NH, 20:1) to afford pure product as pale yellow solid. $^1$H NMR (CDCl$_3$): δ 8.21 (d, 2H), 7.55 (d, 2H), 3.04 (t, 2H, J=7.8), 2.56 (t, 2H, J=7.8), 2.36 (m, 6H), 1.72 (m, 2H), 1.36 (m, 6H), 0.90 (t, 6H, J=7.8). MS (CI) m/z 292 (100, M$^+$). $^{13}$C NMR NMR (CDCl$_3$): δ 148.3, 144.29, 129.93, 118.22, 60.32, 31.67, 32.27, 32.20, 20.81, 13.67. Anal. Calculated for C$_{17}$H$_{28}$N$_2$O$_2$: C, 69.83; H, 9.65; N, 9.58%. Found: C, 69.86; H, 10.12; N, 9.53%

Preparation of Rat Liver and Guinea Pig Liver Membranes.

Minced frozen rat livers or guinea pig livers (65 g) were thawed in 100 mL homogenization buffer (10 mM phosphate buffer pH 7.4 containing 0.32M sucrose, 1 M MgSO$_4$, 0.5 M EGTA, 1 mM phenylmethylsulphonyl fluoride (PMSF), 10 μg/mlleupeptin, 1 μg/ml pepstatin A, 10 μg/ml p-toluenesulfonyl-L-arginine methyl ester (TAME) and then homogenized on ice with a Brinkman polytron homogenizer (setting 6, 4 bursts of 10 second each) followed by a glass homogenizer (Teflon pestle by 6 slow passes at 3,000 rpm). The homogenized tissues were then centrifuged at 17,000 g for 10 minutes. The supernatants were re-centrifuged at 100,000 g for 1 hour. The microsomal pellets were resuspended in homogenization buffer, snap frozen with dry ice-ethanol, and stored at –80° C. at a final protein concentration of 20 mg/mL.

Sigma Receptor Binding Assays.

Competitive binding assays were performed to determine binding affinities of the compounds listed for the sigma-1 and sigma-2 receptors as previously described (Matsumoto et al., *Eur J Pharmacol* 1995, 280, 301; Nguyen et al., *Neuropharmacology* 2005, 49, 638). Assays for sigma-1 were performed using 10 nM (+)-[$^3$H]pentazocine in guinea pig liver homogenates (25 μg/well) incubated at 30° C. for 1 hour with several concentrations of competing ligands. After incubation, membranes were harvested on a 0.5% PEI-treated Whatman GF/B filters using a Brandel Cell Harvester. (+)-[$^3$H] pentazocine binding was determined by liquid scintillation counting. The assay for determining the sigma-2 binding property of IAF was performed using rat liver membranes (25 μg/well) and 3 nM [$^3$H]-DTG in the presence of 100 nM (+)-pentazocine. Serial concentrations of the compounds evaluated were added to the reactions for 45 minutes at 30° C. and the samples vacuum filtered through 0.5% polyethyleneimine (PEI) treated Whatman GF/B as described above to measure displacement of the radioligands from the sigma receptor subtypes. Haloperidol (5 μM) was used to determine non-specific binding for both sigma-1 and sigma-2 receptor binding assays. Radioactivity on the filters was detected by liquid scintillation spectrometry using NEN formula 989 as scintillation cocktail. Values were fit to a non-linear regression curve using graphing software (Graphpad Prism) and reported dissociation equilibrium constants, K$_D$, were calculated using the Cheng-Prussof equation (Cheng, Y.; Prusoff, W. H. *Biochem Pharmacol* 1973, 22, 3099).

Cytotoxicity Assays.

Multi-plex cytotoxicity assays were performed by the Keck-UWCCC Small Molecule Screening Facility (Madison, Wis.). Specific methodology can be found online at http://hts.wisc.edu/Resources.htm#mpa.

Example 7

Alkylamine Compounds

Figure 10:
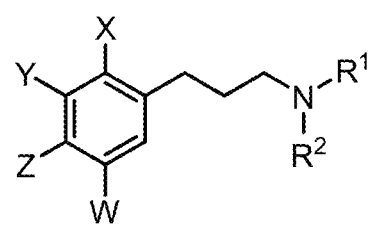
FIG. 10. Compounds 1-3; examples of compounds that include more than one $R^3$ group, according to an embodiment. The butyl groups of $R^1$ and $R^2$ can also be replaced with any ($C_1$-$C_{14}$)alkyl, optionally terminated with an F or $^{18}$F group. Groups X, Y, Z, and W can each independently be any halo or nitro group.

Additional examples of compounds of the invention are illustrated in FIGS. 10 and 11. According to various embodiments, the variables W, X, Y, and Z can be any value defined for R$^3$ in formula I, and R$^1$ and R$^2$ can also have any value defined for R$^1$ and R$^2$ in formula I. The aryl ring of the compound in FIG. 10 can also be penta-substituted, for example, with an additional R$^3$ group. Additionally, any alkyl or aryl group of R$^1$ and R$^2$ can be terminated with a halogen isotope, such as $^{18}$F or $^{125}$I. Such compounds can be useful as diagnostic agents and/or useful for imaging tumors and tumor cells. The hydrogen of the indole compound illustrated in FIG. 11 can be replaced with an R$^1$ group as defined for formula I, or by a nitrogen protecting group, such as a benzyl or trifluoroacetyl group.

The Ruoho laboratory discovered that electron withdrawing groups, such as fluoro and/or nitro groups, on the aryl and indole rings (e.g., aromatic rings of compounds of formula I, and of the structures described by FIGS. 10 and 11) increase the binding affinity of compounds to the Sigma-1 receptor. Singly or multiply fluorinated and/or nitrated phenylpropyl (PP) amine and indole ring compounds can provide increased affinity and highly selective binding to the Sigma-1 receptor. The addition of alkyl chains to the primary nitrogen on the PP amine or the indole alkyl side chain can further enhance affinity for the Sigma-1 receptor.

Methods for preparing fluorinated indole derivatives of tryptophan are known in the art (see for example, Zhong et al., Proc. Natl. Acad. Sci. (1998) 95, 12088-12093). Methods for introducing $^{18}F$ into small molecules are also well known, for example, in the imaging literature. For example, introducing $^{18}F$ can be carried out by displacement of an alkyl trifluoromethyl sulphonyl leaving group (e.g., a triflate) with a caged $^{18}F$ produced by synchrotron bombardment of $^{19}F$ in acetonitrile. The $^{18}F$ compounds can be used to image tumors and other medically relevant conditions involving Sigma-1 receptor mediated functions.

The PP amine and indole compounds can be antagonists or agonists for the Sigma-1 receptor. As such, the PP amine and indole compounds can be used for regulation of functional activities of the Sigma-1 receptor. Such regulation can include treatment of drug addiction and/or treatment of cancer using the compounds as cancer chemotherapeutic agents.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula XI:

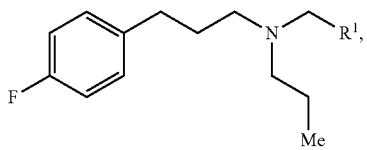

wherein
$R^1$ is substituted phenyl, or substituted benzyl; and
when $R^1$ is phenyl, the phenyl of $R^1$ is substituted with one to five halo, amino, azido, alkyl, or trifluoromethyl groups, or a combination thereof;
when $R^1$ is benzyl, the benzyl of $R^1$ is substituted with:
one to five amino, azido, or alkyl groups, or a combination thereof;
one to four azido groups and one to four halo, amino, alkyl, or trifluoromethyl groups, or a combination thereof;
one to four alkyl groups and one to four halo, amino, azido, or trifluoromethyl groups, or a combination thereof;
two to four amino groups and one to three halo, azido, alkyl, or trifluoromethyl groups, or a combination thereof;
three to five halo groups and one to two amino, azido, alkyl, or trifluoromethyl groups, or a combination thereof; or
three to five trifluoromethyl groups and one to two halo, amino, azido, or alkyl groups, or a combination thereof;
or a salt thereof.

2. The compound of claim 1 wherein the compound exhibits selectivity for the σ-1 receptor over the σ-2 receptor.

3. The compound of claim 1 wherein the compound exhibits selectivity for the σ-2 receptor over the σ-1 receptor and the σ-2 $K_D$:σ-1 $K_D$ ratio is about 0.4 or less.

4. A pharmaceutical composition comprising a compound of claim 1 and a pharmaceutically acceptable diluent or carrier.

5. A compound of claim 1 wherein the compound is:

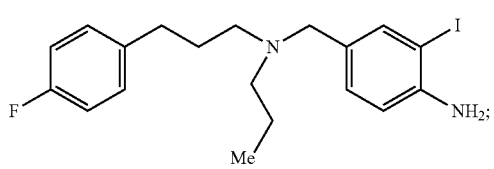

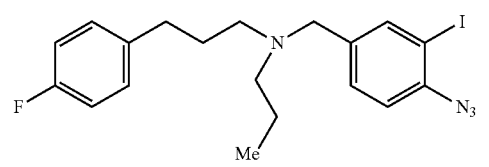

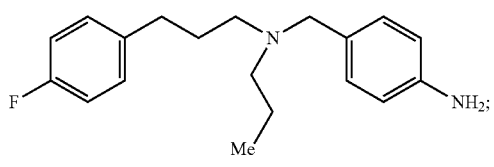

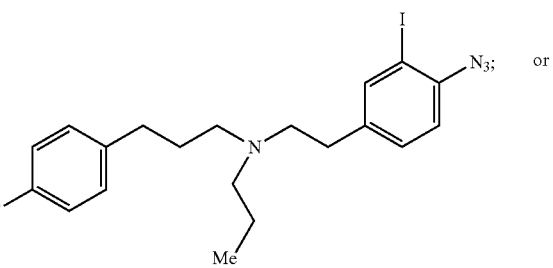

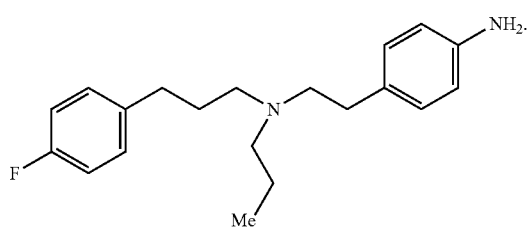

6. A pharmaceutical composition comprising a compound of claim 5 and a pharmaceutically acceptable diluent or carrier.

7. A method of modulating a sigma-1 receptor in a mammal comprising administering to the mammal an effective amount of a compound of claim 1, so that the sigma-1 receptor is modulated, wherein the modulating comprises agonism of the sigma-1 receptor or antagonism of the sigma-1 receptor.

8. The compound of claim 1 wherein $R^1$ is substituted phenyl.

9. The compound of claim 8 wherein the phenyl of $R^1$ is substituted with an amino group.

10. The compound of claim 8 wherein the phenyl of $R^1$ is substituted with a halo group.

11. The compound of claim 10 wherein the phenyl of $R^1$ is substituted with an iodo group.

12. The compound of claim 11 wherein the phenyl of $R^1$ is substituted with an amino group.

13. The compound of claim 1 wherein $R^1$ is substituted benzyl.

14. The compound of claim 13 wherein the benzyl of R¹ is substituted with a halo group.

15. The compound of claim 14 wherein the benzyl of R¹ is substituted with an iodo group.

16. The compound of claim 13 wherein the benzyl of R¹ is substituted with an azido group or an amino group.

17. A compound of claim 1 wherein the compound is:

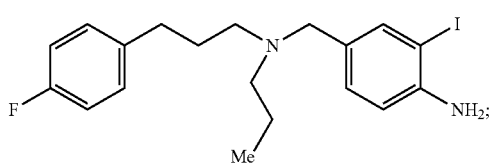
14

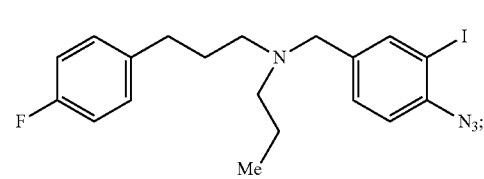
15

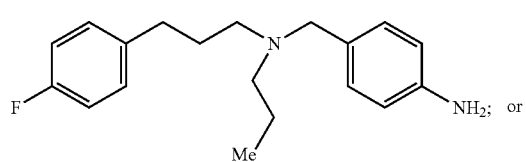
17

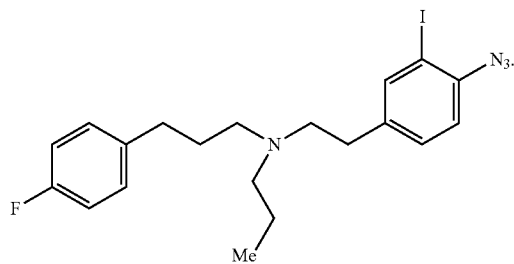
19

18. A compound of claim 1 wherein the compound is:

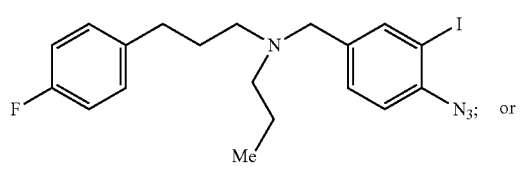
15

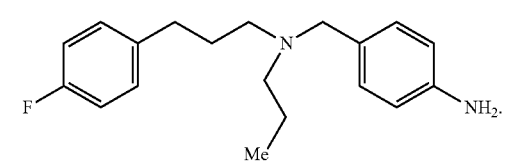
17

19. A compound of claim 1 wherein R¹ is benzyl, and the benzyl of R¹ is substituted with one to five azido or alkyl groups, or a combination thereof.

* * * * *